(12) United States Patent
Mishima

(10) Patent No.: US 10,779,714 B2
(45) Date of Patent: Sep. 22, 2020

(54) IMAGE PROCESSING APPARATUS, METHOD FOR OPERATING IMAGE PROCESSING APPARATUS, AND IMAGE PROCESSING PROGRAM

(71) Applicant: FUJIFILM Corporation, Tokyo (JP)

(72) Inventor: Takahiro Mishima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 108 days.

(21) Appl. No.: 16/140,561

(22) Filed: Sep. 25, 2018

(65) Prior Publication Data

US 2019/0021580 A1 Jan. 24, 2019

Related U.S. Application Data

(63) Continuation of application No. PCT/JP2017/012038, filed on Mar. 24, 2017.

(30) Foreign Application Priority Data

Mar. 29, 2016 (JP) .................. 2016-064853

(51) Int. Cl.
*G06K 9/00* (2006.01)
*A61B 1/045* (2006.01)
(Continued)

(52) U.S. Cl.
CPC .............. *A61B 1/045* (2013.01); *A61B 1/00* (2013.01); *A61B 1/00009* (2013.01);
(Continued)

(58) Field of Classification Search
CPC ..................................... A61B 1/045
See application file for complete search history.

(56) References Cited

U.S. PATENT DOCUMENTS 8,743,189 B2   6/2014  Kitamura
9,468,356 B2  10/2016  Ikemoto et al.
(Continued)

FOREIGN PATENT DOCUMENTS

CN      101803899      8/2010
CN      104116485     10/2014
(Continued)

OTHER PUBLICATIONS

Imtiaz et al (NPL "Color Enhancement in Endoscopic Images Using Adaptive Sigmoid Function and Space Variant Color Reproduction", vol. 2015, Article ID 607407, 19 pages http://dx.doi.org/10.1155/2015/607407). (Year: 2015).*

(Continued)

*Primary Examiner* — Oneal R Mistry
(74) *Attorney, Agent, or Firm* — JCIPRNET

(57) ABSTRACT

An endoscopic image formed by an image signal including a narrow-band image signal is acquired. The brightness, hue and saturation of each pixel of the endoscopic image are calculated. The hue H of each pixel of the endoscopic image is changed to a hue H+ΔH that is away from the hue of a reference color indicating a normal part and the saturation S of each pixel is changed to a saturation S+ΔS that is away from the saturation of the reference color that is determined according to the brightness of each pixel of the endoscopic image. The endoscopic image in which the brightness of each pixel is the original brightness and which has a color having converted hue and saturation is output.

19 Claims, 8 Drawing Sheets

(51) Int. Cl.
  *H04N 7/18* (2006.01)
  *A61B 1/00* (2006.01)
  *A61B 1/05* (2006.01)
  *H04N 5/225* (2006.01)

(52) U.S. Cl.
  CPC .............. *A61B 1/051* (2013.01); *H04N 7/18* (2013.01); *H04N 2005/2255* (2013.01)

(56) References Cited

U.S. PATENT DOCUMENTS

| | | | |
|---|---|---|---|
| 9,582,878 | B2 | 2/2017 | Kuramoto |
| 9,595,085 | B2 | 3/2017 | Kuramoto et al. |
| 2006/0082647 | A1 | 4/2006 | Donomae et al. |
| 2008/0284845 | A1 | 11/2008 | Aach et al. |
| 2009/0290068 | A1 | 11/2009 | Abe et al. |
| 2012/0316421 | A1* | 12/2012 | Kumar ............... A61B 1/00009 600/407 |
| 2013/0121546 | A1* | 5/2013 | Guissin ................ G06T 7/0012 382/128 |
| 2015/0193929 | A1* | 7/2015 | Ikemoto ............... G06T 7/0012 382/128 |
| 2015/0269750 | A1 | 9/2015 | Moriya |
| 2015/0379698 | A1 | 12/2015 | Kuramoto et al. |
| 2016/0007829 | A1 | 1/2016 | Chun |
| 2016/0029925 | A1 | 2/2016 | Kuramoto et al. |
| 2017/0155804 | A1 | 6/2017 | Kikuchi |

FOREIGN PATENT DOCUMENTS

| | | |
|---|---|---|
| CN | 105101862 | 11/2015 |
| DE | 102014105826 | 11/2014 |
| EP | 2875775 | 5/2015 |
| JP | H02134091 | 5/1990 |
| JP | 2000092337 | 3/2000 |
| JP | 2002281327 | 9/2002 |
| JP | 2006142001 | 6/2006 |
| JP | 2008072252 | 3/2008 |
| JP | 2014018332 | 2/2014 |
| JP | 2015192840 | 11/2015 |
| JP | 2016010506 | 1/2016 |
| WO | 2014156938 | 10/2014 |
| WO | 2015064435 | 5/2015 |
| WO | 2016006429 | 1/2016 |

OTHER PUBLICATIONS

"Search Report of Europe Counterpart Application", dated Feb. 21, 2019, p. 1-p. 9.

"Written Opinion of the International Searching Authority (Form PCT/ISA/237) of PCT/JP2017/012038," dated Aug. 1, 2017, with English translation thereof, pp. 1-10.

"International Search Report (Form PCT/ISA/210) of PCT/JP2017/012038," dated Aug. 1, 2017, with English translation thereof, pp. 1-5.

"Office Action of Japan Counterpart Application," with English translation thereof, dated Feb. 12, 2020, p. 1-p. 6.

"Office Action of China Counterpart Application", dated May 29, 2020, with English translation thereof, p. 1-p. 12.

"Office Action of Japanese Counterpart Application," dated Jul. 21, 2020, with English translation thereof, p. 1-p. 4.

* cited by examiner (A)

(B)

(C)

(D)

IMAGE PROCESSING APPARATUS, METHOD FOR OPERATING IMAGE PROCESSING APPARATUS, AND IMAGE PROCESSING PROGRAM

CROSS-REFERENCE TO RELATED APPLICATIONS

This application is a continuation application of International Application No. PCT/JP2017/012038, filed on Mar. 24, 2017, which is incorporated herein by reference in its entirety. Further, this application claims priority from Japanese Patent Application No. 2016-064853, filed on Mar. 29, 2016, the disclosure of which is incorporated by reference herein in its entirety.

BACKGROUND

Technical Field

The present invention relates to an image processing apparatus, a method for operating an image processing apparatus, and an image processing program that process, for example, an image used at the time of diagnosis of atrophic gastritis.

Related Art

In a medical field, diagnosis using an endoscope system including a light source device, an electronic endoscope, and a processor device has been generally performed. In particular, definite diagnosis before endoscopic therapy, such as endoscope mucosal resection or endoscope submucosal dissection, is performed is needed in a hospital in which gastroenterological endoscopy is performed. There is an increasing need to observe an endoscopic image in which a change in mucosa has been enhanced in order to observe the state of the change in mucosa.

Examples of a method for observing the enhanced change include an optical method, a digital method, an optical digital method, and a pigment dispersion method. For example, Flexible spectral Imaging Color Enhancement (FICE, registered trademark) which is a digital method, Narrow Band Imaging (NBI, registered trademark) which is an optical digital method, or indigo carmine spraying or Lugol spraying which is a pigment dispersion method is used to observe or pick up microscopic blood vessels in a surface structure. In general, the endoscope captures an image using white light. In FICE, signal processing is performed to extract a spectral image, which makes it easy to see, for example, tissue properties or blood vessels. In contrast, in NBI, the band of white light is narrowed by an optical filter, narrow-band light is emitted, reflection spectrum information of a living body is acquired, and an enhanced image is displayed.

In recent years, the performance of a color endoscopic device has been improved and it is possible to distinguish a site of lesion that is slightly different from a normal tissue in color. However, in an endoscopic image, the focus tends to be put on a red part and a change in color at the boundary between a normal mucosa tissue and a site of lesion is continuous. Therefore, it is difficult for an unskilled technician to distinguish a difference in color between the site of lesion and the normal mucosa tissue. In JP2014-018332A, the color space of endoscopic image data is converted into an HSI color space based on hue, saturation, and intensity or an HSV color space based on hue, saturation, and value, it is determined whether a pixel of a site of lesion is present on the basis of the hue and the saturation, and the color of a pixel that is determined as the pixel of the site of lesion is changed, which makes it easy to recognize the site of lesion.

In the endoscope using the light whose band has been narrowed, light with a wavelength that is likely to be absorbed by hemoglobin in blood is emitted and observation is performed. Therefore, an endoscopic image in which capillaries in a superficial layer of mucosa and a fine mucosal pattern have been enhanced is obtained. In a case in which gastric mucosa is normal in the endoscopic image, since a mucosal layer in the surface is thick, most of light is absorbed by the mucosal layer and is then reflected and blood vessels in a normal gastric submucosal layer are hardly observed from the endoscopic image. In contrast, in the case of gastric mucosa in which atrophic gastritis has progressed, the mucosal layer is thinned by a reduction in the number of gastric gland cells. With the progress of the atrophic gastritis, the internal structure of the gastric mucosa is changed. On the endoscopic image, muscularis mucosa of a color close to white is seen and the color of the atrophic mucosal part is more faded than the color of the normal part. In addition, in the atrophic mucosal part, the mucosal layer is thinned due to atrophy and blood vessels in the submucosal layer are seen. Therefore, in the diagnosis of a site of gastric lesion based on atrophic gastritis, the degree of progress of atrophy or the boundary between a normal part and a gastritis part is determined using the above-mentioned characteristics.

However, in the endoscope using the light whose band has been narrowed, in a case in which atrophy has been highly advanced (for example, in the case of atrophy included in a C group or a D group in ABC examination), it is possible to clearly observe the above-mentioned characteristics on the endoscopic image. However, in a case in which atrophy is not highly advanced (for example, in the case of atrophy included in a B group or a C group in ABC examination), there is little difference between an atrophic part and a normal part on the endoscopic image and it may be difficult to determine the degree of progress of atrophy or the boundary between the normal part and the gastritis part. Therefore, it is necessary to clarify the difference caused by the above-mentioned characteristics on the endoscopic image such that the boundary between the normal part and the gastritis part can be observed.

In a case in which a tubular structure is captured, since a part that is in front of the tubular structure in a depth direction is close to a light source, the image of the part becomes a bright image. However, since a part that is behind the tubular structure in the depth direction is far away from the light source, the image of the part becomes a dark image. In the dark image, a difference in hue and saturation between normal mucosa and abnormal mucosa is different from that in the bright image and the boundary between a normal part and an abnormal part is not necessarily clearly defined by the same hue and saturation correction as that in the bright image.

SUMMARY

An object of the invention is to provide an image processing apparatus, a method for operating an image processing apparatus, and an image processing program that can enhance a change in the color of, for example, mucosa which is likely to occur in a case in which the stomach is atrophied due to atrophic gastritis.

According to the invention, there is provided an image processing apparatus comprising: an image acquisition unit that acquires an endoscopic image formed by an image signal including a narrow-band image signal; a color information calculation unit that calculates brightness, hue, and saturation of each pixel of the endoscopic image; a first color difference expansion unit that changes the hue of each pixel of the endoscopic image such that a difference between the hue of the pixel and the hue of a reference color indicating a normal part is more than a difference between an original hue and the hue of the reference color in a case in which the difference between the hue of the reference color and the hue of the pixel is within a first range and changes the hue of the pixel to the original hue in a case in which the hue of each pixel is matched with the hue of the reference color and a case in which the hue difference is beyond the first range; a second color difference expansion unit that changes the saturation of each pixel such that a difference between the saturation of the pixel and the saturation of the reference color which is determined according to the brightness of each pixel of the endoscopic image is more than a difference between an original saturation and the saturation of the reference color in a case in which the difference between the saturation of the reference color and the saturation of the pixel is within a second range and changes the saturation of the pixel to the original saturation in a case in which the saturation of each pixel is matched with the saturation of the reference color and a case in which the saturation difference is beyond the second range; and an output unit that outputs an endoscopic image in which the brightness of each pixel is the original brightness and whose color has been changed to a color having the hue obtained by the first color difference expansion unit and the saturation obtained by the second color difference expansion unit.

According to the invention, there is provided a method for operating an image processing apparatus comprising an image acquisition unit, a color information calculation unit, a first color difference expansion unit, a second color difference expansion unit, and a output unit. The method comprises: an image acquisition step of allowing the image acquisition unit to acquire an endoscopic image formed by an image signal including a narrow-band image signal; a color information calculation step of allowing the color information calculation unit to calculate brightness, hue, and saturation of each pixel of the endoscopic image; a first color difference expansion step of allowing the first color difference expansion unit to change the hue of each pixel of the endoscopic image such that a difference between the hue of the pixel and the hue of a reference color indicating a normal part is more than a difference between an original hue and the hue of the reference color in a case in which the difference between the hue of the reference color and the hue of the pixel is within a first range and to change the hue of the pixel to the original hue in a case in which the hue of each pixel is matched with the hue of the reference color and a case in which the hue difference is beyond the first range; a second color difference expansion step of allowing the second color difference expansion unit to change the saturation of each pixel such that a difference between the saturation of the pixel and the saturation of the reference color which is determined according to the brightness of each pixel of the endoscopic image is more than a difference between an original saturation and the saturation of the reference color in a case in which the difference between the saturation of the reference color and the saturation of the pixel is within a second range and to change the saturation of the pixel to the original saturation in a case in which the saturation of each pixel is matched with the saturation of the reference color and a case in which the saturation difference is beyond the second range; and an output step of allowing the output unit to output an endoscopic image in which the brightness of each pixel is the original brightness and whose color has been changed to a color having the hue obtained by the first color difference expansion unit and the saturation obtained by the second color difference expansion unit.

According to the invention, there is provided an image processing program that causes a computer to function as: an image acquisition unit that acquires an endoscopic image formed by an image signal including a narrow-band image signal; a color information calculation unit that calculates brightness, hue, and saturation of each pixel of the endoscopic image; a first color difference expansion unit that changes the hue of each pixel of the endoscopic image such that a difference between the hue of the pixel and the hue of a reference color indicating a normal part is more than a difference between an original hue and the hue of the reference color in a case in which the difference between the hue of the reference color and the hue of the pixel is within a first range and changes the hue of the pixel to the original hue in a case in which the hue of each pixel is matched with the hue of the reference color and a case in which the hue difference is beyond the first range; a second color difference expansion unit that changes the saturation of each pixel such that a difference between the saturation of the pixel and the saturation of the reference color which is determined according to the brightness of each pixel of the endoscopic image is more than a difference between an original saturation and the saturation of the reference color in a case in which the difference between the saturation of the reference color and the saturation of the pixel is within a second range and changes the saturation of the pixel to the original saturation in a case in which the saturation of each pixel is matched with the saturation of the reference color and a case in which the saturation difference is beyond the second range; and an output unit that outputs an endoscopic image in which the brightness of each pixel is the original brightness and whose color has been changed to a color having the hue obtained by the first color difference expansion unit and the saturation obtained by the second color difference expansion unit.

The "narrow-band image signal" means an image signal obtained by capturing an image of a specimen irradiated with narrow-band light and the "image signal including the narrow-band image signal" means an image signal obtained by capturing an image of a specimen irradiated with light including the narrow-band light.

The "brightness" means a color component indicating luminance. Similarly to the brightness, lightness is used as a component indicating luminance. Color spaces include a color space that has a coordinate axis of a component indicated by brightness and a color space that has a coordinate axis of a component indicated by lightness. In the specification, both the brightness and the lightness are components indicating luminance and are not distinguished from each other.

The "changing the hue of the pixel such that a difference between a changed hue and the hue of the reference color is more than a difference between an original hue and the hue of the reference color" means that, in a case in which the hue of the pixel has a larger value than the hue of reference color, the hue of the pixel is changed such the hue of the pixel is even more than the hue of the reference color and, in a case in which the hue of the pixel has a smaller value than the hue of reference color, the hue of the pixel is changed such the hue of the pixel is even less than the hue of the reference color.

The "changing the saturation of the pixel such that a difference between a changed saturation and the saturation of the reference color is more than a difference between an original saturation and the saturation of the reference color" means that, in a case in which the saturation of the pixel has a larger value than the saturation of reference color, the saturation of the pixel is changed such the saturation of the pixel is even more than the saturation of the reference color and, in a case in which the saturation of the pixel has a smaller value than the saturation of reference color, the saturation of the pixel is changed such the saturation of the pixel is even less than the saturation of the reference color.

The "first range" means the range of the hue of a pixel having a color, which appears in a case in which an image of an imaging target is captured, in the endoscopic image. In a case in which the hue is beyond the range, the color can be determined to be different from the original color of the imaging target. For example, in the case of the image of the inner wall of the stomach, the hue of a color included in the color of the inner wall of the stomach is within the first range and the hue of a color that is different from the color of the inner wall of the normal stomach, for example, the color of a pigment or residues dispersed in the stomach is beyond the first range.

The "second range" means the range of the saturation of a pixel having a color, which appears in a case in which an image of an imaging target is captured, in the endoscopic image. In a case in which the saturation is beyond the range, the color can be determined to be different from the original color of the imaging target. For example, in the case of the image of the inner wall of the stomach, the saturation of a color included in the color of the inner wall of the stomach is within the second range and the saturation of a color that is different from the color of the inner wall of the normal stomach, for example, the color of a pigment or residues dispersed in the stomach is beyond the second range.

Preferably, the first color difference expansion unit increases an amount of expansion for changing the original hue of each pixel to the changed hue as the hue difference increases in a case in which the hue difference is less than a first difference value within the first range and decreases the amount of expansion for changing the original hue of each pixel to the changed hue as the hue difference increases in a case in which the hue difference is greater than the first difference value.

Preferably, the second color difference expansion unit increases an amount of expansion for changing the original saturation of each pixel to the changed saturation as the saturation difference increases in a case in which the saturation difference is less than a second difference value within the second range and decreases the amount of expansion for changing the original saturation of each pixel to the changed saturation as the saturation difference increases in a case in which the saturation difference is greater than the second difference value.

Preferably, the saturation of the reference color increases as the brightness of each pixel increases and the saturation of the reference color decreases as the brightness of each pixel decreases.

Preferably, the amount of expansion for changing the original saturation of each pixel to the changed saturation reaches a peak in a case in which the saturation difference is the second difference value and the second color difference expansion unit increases the peak as the saturation of the reference color increases and decreases the peak as the saturation of the reference color decreases.

Preferably, the second color difference expansion unit widens the second range as the saturation of the reference color increases and narrows the second range as the saturation of the reference color decreases.

Preferably, the hue of the reference color is constant even in a case in which a brightness value of each pixel varies.

The brightness of each pixel may be an average of the brightness of pixels in a predetermined range having the pixel as a center.

The brightness of each pixel may be calculated from the brightness of pixels which are present at positions corresponding to each pixel in a low-resolution image of the endoscopic image.

Preferably, the narrow-band image signal is obtained by capturing an image of a specimen illuminated with narrow-band light which is absorbed by blood at a higher rate than light in other bands.

Preferably, the narrow-band image signal is a blue narrow-band image signal obtained by capturing an image of a specimen illuminated with blue narrow-band light, which is absorbed by blood at a higher rate than light in other bands, in a blue band or a green narrow-band image signal obtained by capturing an image of a specimen illuminated with green narrow-band light, which is absorbed by blood at a higher rate than light in other bands, in a green band.

The endoscopic image may be an image of an inner wall of a stomach, the normal part may be a normal mucosa, and an abnormal part may be an abnormal mucosa.

The first color difference expansion unit may determine the hue of each pixel on the basis of a hue-hue conversion table in which a value for changing the original hue to the changed hue is defined. The second color difference expansion unit may store a plurality of saturation-saturation conversion tables, in which a value for changing the original saturation to the changed saturation is defined, according to different brightness values in advance and may determine the saturation of each pixel on the basis of a saturation-saturation conversion table corresponding to the brightness of each pixel among the plurality of saturation-saturation conversion tables.

According to the invention, there is provided another image processing apparatus comprising: an image acquisition unit that acquires an endoscopic image formed by an image signal including a narrow-band image signal; a color information calculation unit that calculates brightness, hue, and saturation of each pixel of the endoscopic image; a first color difference expansion unit that (i) changes the hue of each pixel of the endoscopic image such that a difference between a changed hue and the hue of a reference color indicating a normal part is more than a difference between an original hue and the hue of the reference color in a case in which a difference between the hue of the reference color and the hue of the pixel is within a first range and changes the hue of the pixel to the original hue in a case in which the hue of each pixel is matched with the hue of the reference color and a case in which the hue difference is beyond the first range, and (ii) increases an amount of expansion for changing the original hue of each pixel to the changed hue as the hue difference increases in a case in which the hue difference is less than a first difference value, which is a difference in hue between an abnormal part and the normal part, within the first range and decreases the amount of expansion for changing the original hue of each pixel to the changed hue as the hue difference increases in a case in which the hue difference is greater than the first difference value; a second color difference expansion unit that (i) changes the saturation of each pixel such that a difference between a changed saturation and the saturation of the reference color which is determined according to the brightness of each pixel of the endoscopic image is more than a difference between an original saturation and the saturation of the reference color in a case in which a difference between the saturation of the reference color and the saturation of the pixel is within a second range and changes the saturation of the pixel to the original saturation in a case in which the saturation of each pixel is matched with the saturation of the reference color and a case in which the saturation difference is beyond the second range, and (ii) increases an amount of expansion for changing the original saturation of each pixel to the changed saturation as the saturation difference increases in a case in which the saturation difference is less than a second difference value, which is a difference in saturation between the abnormal part and the normal part, within the second range and decreases the amount of expansion for changing the original saturation of each pixel to the changed saturation as the saturation difference increases in a case in which the saturation difference is greater than the second difference value; and an output unit that outputs an endoscopic image in which the brightness of each pixel is the original brightness and whose color has been changed to a color having the hue obtained by the first color difference expansion unit and the saturation obtained by the second color difference expansion unit. As the brightness of each pixel increases, the saturation of the reference color increases. As the brightness of each pixel decreases, the saturation of the reference color decreases. The amount of expansion for changing the original saturation of each pixel to the changed saturation reaches a peak in a case in which the saturation difference is the second difference value and the second color difference expansion unit increases the peak as the saturation of the reference color increases and decreases the peak as the saturation of the reference color decreases.

According to the invention, there is provided another method for operating an image processing apparatus comprising an image acquisition unit, a color information calculation unit, a first color difference expansion unit, a second color difference expansion unit, and an output unit. The method comprises: an image acquisition step of allowing the image acquisition unit to acquire an endoscopic image formed by an image signal including a narrow-band image signal; a color information calculation step of allowing the color information calculation unit to calculate brightness, hue, and saturation of each pixel of the endoscopic image; a first color difference expansion step of allowing the first color difference expansion unit (i) to change the hue of each pixel of the endoscopic image such that a difference between a changed hue and the hue of a reference color indicating a normal part is more than a difference between an original hue and the hue of the reference color in a case in which a difference between the hue of the reference color and the hue of the pixel is within a first range and to change the hue of the pixel to the original hue in a case in which the hue of each pixel is matched with the hue of the reference color and a case in which the hue difference is beyond the first range and (ii) to increase an amount of expansion for changing the original hue of each pixel to the changed hue as the hue difference increases in a case in which the hue difference is less than a first difference value, which is a difference in hue between an abnormal part and the normal part, within the first range and to decrease the amount of expansion for changing the original hue of each pixel to the changed hue as the hue difference increases in a case in which the hue difference is greater than the first difference value; a second color difference expansion step of allowing the second color difference expansion unit (i) to change the saturation of each pixel such that a difference between a changed saturation and the saturation of the reference color which is determined according to the brightness of each pixel of the endoscopic image is more than a difference between an original saturation and the saturation of the reference color in a case in which a difference between the saturation of the reference color and the saturation of the pixel is within a second range and to change the saturation of the pixel to the original saturation in a case in which the saturation of each pixel is matched with the saturation of the reference color and a case in which the saturation difference is beyond the second range, and (ii) to increase an amount of expansion for changing the original saturation of each pixel to the changed saturation as the saturation difference increases in a case in which the saturation difference is less than a second difference value, which is a difference in saturation between the abnormal part and the normal part, within the second range and to decrease the amount of expansion for changing the original saturation of each pixel to the changed saturation as the saturation difference increases in a case in which the saturation difference is greater than the second difference value; and an output step of allowing the output unit to output an endoscopic image in which the brightness of each pixel is the original brightness and whose color has been changed to a color having the hue obtained by the first color difference expansion unit and the saturation obtained by the second color difference expansion unit. As the brightness of each pixel increases, the saturation of the reference color increases. As the brightness of each pixel decreases, the saturation of the reference color decreases. In the second color difference expansion step, the amount of expansion for changing the original saturation of each pixel to the changed saturation reaches a peak in a case in which the saturation difference is the second difference value and the peak increases as the saturation of the reference color increases and decreases as the saturation of the reference color decreases.

According to the invention, there is provided another image processing program that causes a computer to function as: an image acquisition unit that acquires an endoscopic image formed by an image signal including a narrow-band image signal; a color information calculation unit that calculates brightness, hue, and saturation of each pixel of the endoscopic image; a first color difference expansion unit that (i) changes the hue of each pixel of the endoscopic image such that a difference between a changed hue and the hue of a reference color indicating a normal part is more than a difference between an original hue and the hue of the reference color in a case in which a difference between the hue of the reference color and the hue of the pixel is within a first range and changes the hue of the pixel to the original hue in a case in which the hue of each pixel is matched with the hue of the reference color and a case in which the hue difference is beyond the first range, and (ii) increases an amount of expansion for changing the original hue of each pixel to the changed hue as the hue difference increases in a case in which the hue difference is less than a first difference value, which is a difference in hue between an abnormal part and the normal part, within the first range and decreases the amount of expansion for changing the original hue of each pixel to the changed hue as the hue difference increases in a case in which the hue difference is greater than the first difference value; a second color difference expansion unit that (i) changes the saturation of each pixel such that a difference between a changed saturation and the saturation of the reference color which is determined according to the brightness of each pixel of the endoscopic image is more than a difference between an original saturation and the saturation of the reference color in a case in which a difference between the saturation of the reference color and the saturation of the pixel is within a second range and changes the saturation of the pixel to the original saturation in a case in which the saturation of each pixel is matched with the saturation of the reference color and a case in which the saturation difference is beyond the second range, and (ii) increases an amount of expansion for changing the original saturation of each pixel to the changed saturation as the saturation difference increases in a case in which the saturation difference is less than a second difference value, which is a difference in saturation between the abnormal part and the normal part, within the second range and decreases the amount of expansion for changing the original saturation of each pixel to the changed saturation as the saturation difference increases in a case in which the saturation difference is greater than the second difference value; and an output unit that outputs an endoscopic image in which the brightness of each pixel is the original brightness and whose color has been changed to a color having the hue obtained by the first color difference expansion unit and the saturation obtained by the second color difference expansion unit. As the brightness of each pixel increases, the saturation of the reference color increases. As the brightness of each pixel decreases, the saturation of the reference color decreases. The amount of expansion for changing the original saturation of each pixel to the changed saturation reaches a peak in a case in which the saturation difference is the second difference value and the second color difference expansion unit increases the peak as the saturation of the reference color increases and decreases the peak as the saturation of the reference color decreases.

The "hue of the abnormal part" and the "saturation of the abnormal part" mean the hue and saturation of the color that is likely to appear in the abnormal part, respectively, and mean hue and saturation representing the color of the abnormal part, respectively. For example, the "hue of the abnormal part" and the "saturation of the abnormal part" may be hue and saturation that most frequently appear in the abnormal part or may be the average color of the abnormal part. In addition, the "saturation of the abnormal part" varies depending on brightness.

According to the invention, the brightness, hue and saturation of each pixel of an endoscopic image that is formed by an image signal including a narrow-band image signal are calculated. The hue of an abnormal part is changed to hue that is separated from the hue of a reference color indicating a normal part on the basis of the hue of the reference color and the saturation of the abnormal part is changed to saturation that is separated from the saturation of the reference color on the basis of the saturation of the reference color. In this way, for example, it is possible to enhance a difference in color between a normal part and an abnormal part, such as mucosa, which is likely to occur in a case in which the stomach is atrophied due to atrophic gastritis. In addition, the saturation of the reference color varies depending on brightness. Therefore, in the case of a tubular structure, it is possible to obtain a clear image without distorting a structure that is in front of the tubular structure in a depth direction and appears in a bright image and a structure that is behind the tubular structure in the depth direction and appears in a dark image.

DETAILED DESCRIPTION

Figure 1:
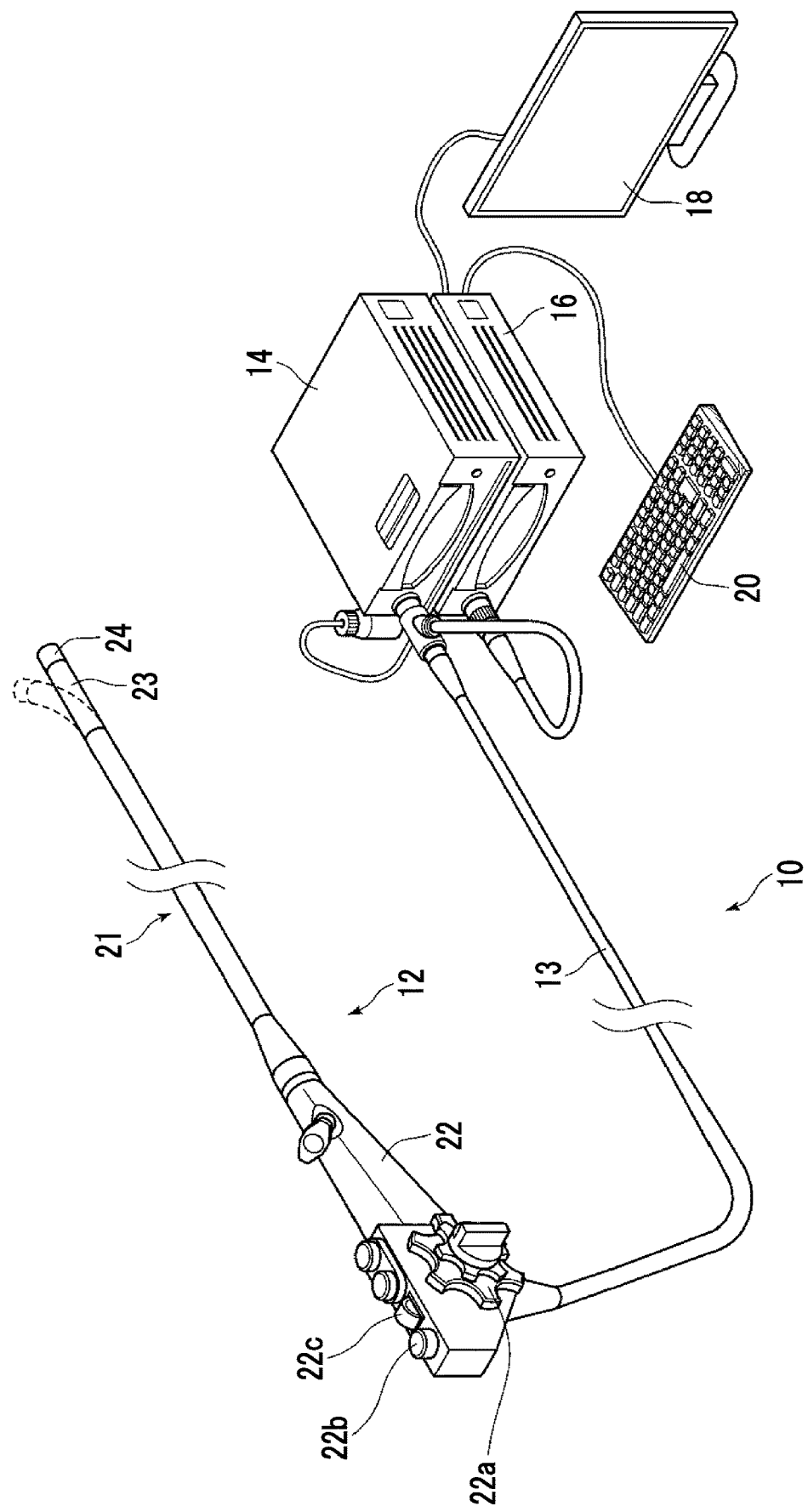
FIG. 1 is a diagram illustrating the outward appearance of an endoscope system.

As illustrated in FIG. 1, an endoscope system 10 according to a first embodiment includes an endoscope 12, a universal cord 13, a light source device 14, a processor device 16, a monitor (display unit) 18, and an input device 20. The endoscope 12 is optically connected to the light source device 14 through the universal cord 13 and is electrically connected to the processor device 16 through the universal cord 13. The endoscope 12 includes an insertion portion 21 that is inserted into a specimen, an operation portion 22 that is provided at a base end of the insertion portion, and a bendable portion 23 and a leading end portion 24 that are provided at the leading end of the insertion portion 21. An angle knob 22a of the operation portion 22 is operated to bend the bendable portion 23. With the bending operation, the leading end portion 24 faces a desired direction.

The operation portion 22 includes a mode switch (mode SW) 22b and a zoom operation portion 22c in addition to the angle knob 22a. The mode switch 22b is used for a switching operation between two types of modes, that is, a normal observation mode and a special observation mode. In the normal observation mode, white light is used to illuminate the inside of the specimen. In the special observation mode, special bluish light is used to illuminate the inside of the specimen and a change in the color of mucosa or the appearance of visible blood vessels which is likely to occur in a case in which the stomach is atrophied due to atrophic gastritis is enhanced. The zoom operation portion 22c is used for a zoom operation for driving a zooming lens 47 (see FIG. 2) in the endoscope 12 to enlarge the specimen.

The processor device 16 is connected to the monitor 18 and the input device 20. The monitor 18 outputs and displays, for example, image information. The input device 20 functions as a user interface that receives, for example, an input operation such as a function setting operation. In addition, an external recording unit (not illustrated) for recording, for example, image information may be connected to the processor device 16.

Figure 2:
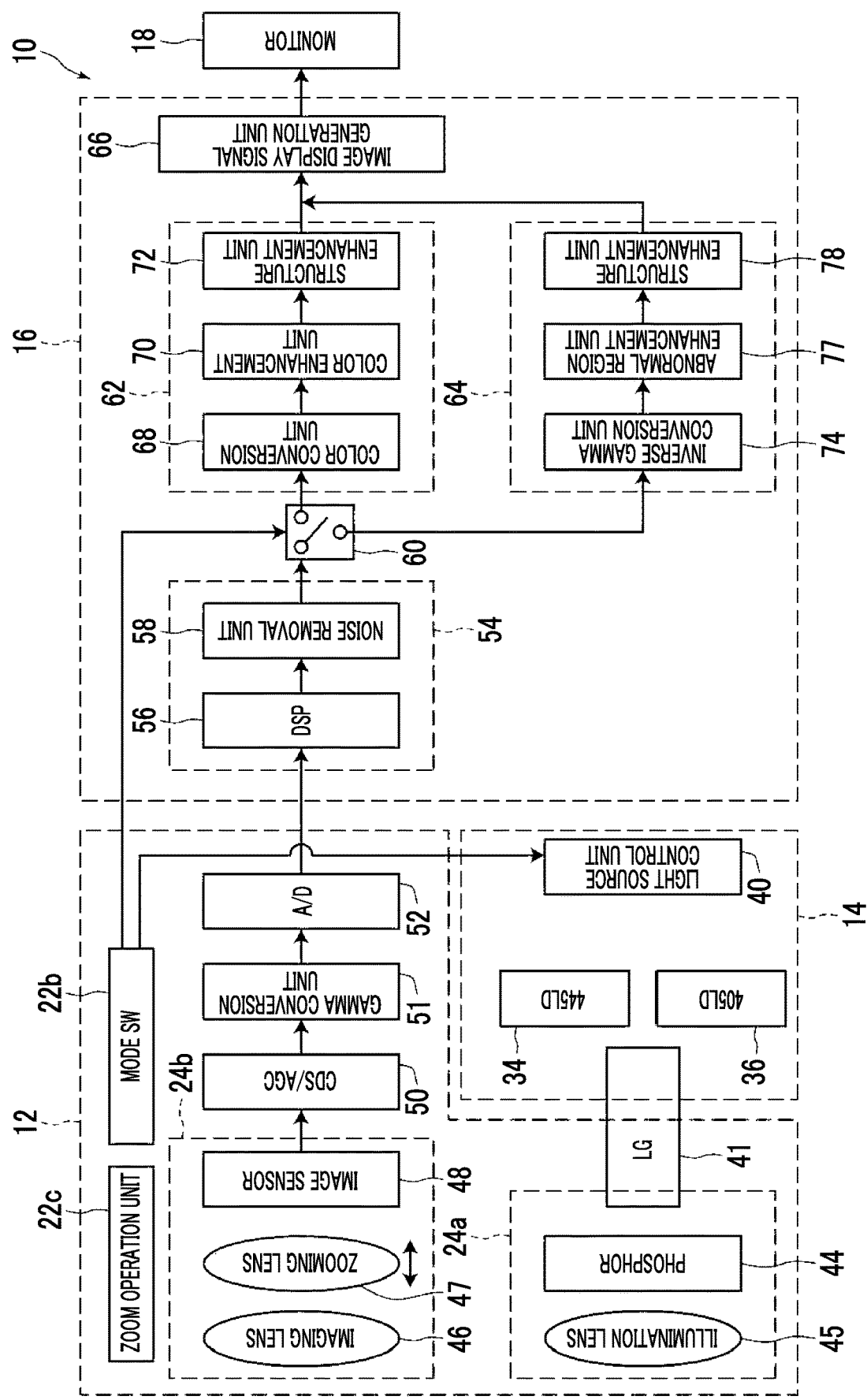
FIG. 2 is a block diagram illustrating the function of an endoscope system according to a first embodiment.

As illustrated in FIG. 2, the light source device 14 has a blue laser light source (445LD) 34 that emits blue laser light with a center wavelength of 445 nm and a blue-violet laser light source (405LD) 36 that emits blue-violet laser light with a center wavelength of 405 nm as light emitting sources. A light source control unit 40 individually controls the emission of light from semiconductor light emitting elements of the light sources 34 and 36. The ratio of the amount of light emitted from the blue laser light source 34 to the amount of light emitted from the blue-violet laser light source 36 is variable. In the normal observation mode, the light source control unit 40 performs control such that the blue laser light source 34 is mainly driven and a small amount of blue-violet laser light is emitted. In the normal observation mode, the blue-violet laser light source 36 may be driven. However, in this case, it is preferable to reduce the emission intensity of the blue-violet laser light source 36.

In contrast, in the special observation mode, the light source control unit 40 performs control such that both the blue laser light source 34 and the blue-violet laser light source 36 are driven and the emission rate of the blue laser light is higher than the emission rate of the blue-violet laser light. In addition, it is preferable that the full width at half maximum of the blue laser light or the blue-violet laser light is about ±10 nm. The blue laser light source 34 and the blue-violet laser light source 36 may be a broad-area InGaN-based laser diode, an InGaAsN-based laser diode, or a GaAsN-based laser diode. In addition, a light emitter, such as a light emitting diode, may be used as the above-mentioned light source.

The laser light emitted from each of the light sources 34 and 36 is incident on a light guide (LG) 41 through optical members (not illustrated) such as a condensing lens, an optical fiber, and a multiplexer. The light guide 41 is provided in the light source device 14, the endoscope 12, and the universal cord (a cord for connecting the endoscope 12 and the light source device 14) 13. Blue laser light with a center wavelength of 445 nm or blue-violet laser light with a center wavelength of 405 nm is propagated to the leading end portion 24 of the endoscope 12 through the light guide 41. In addition, a multi-mode fiber can be used as the light guide 41. For example, a thin fiber cable with a diameter φ of 0.3 mm to 0.5 mm including a core diameter of 105 μm, a clad diameter of 125 μm, and a protective layer as a sheath can be used.

Blue narrow-band light, such as the blue laser light and the blue-violet laser light, is absorbed by a light absorbing material in the mucosa, specifically, blood (particularly, hemoglobin) mainly included in the digestive organs at a high rate and the difference between a normal mucosal region and an atrophic mucosal region is large in a case in which imaging is performed in the special observation mode.

The leading end portion 24 of the endoscope 12 includes an illumination optical system 24a and an imaging optical system 24b. The illumination optical system 24a is provided with a phosphor 44 on which the blue laser light with a center wavelength 445 nm or the blue-violet laser light with a center wavelength of 405 nm from the light guide 41 is incident and an illumination lens 45. In a case in which the phosphor 44 is irradiated with the blue laser light, fluorescent light is emitted from the phosphor 44. In addition, a portion of the blue laser light is transmitted through the phosphor 44. The blue-violet laser light is transmitted without exciting the phosphor 44. The specimen is irradiated with the light emitted from the phosphor 44 through the illumination lens 45.

Figure 3A:
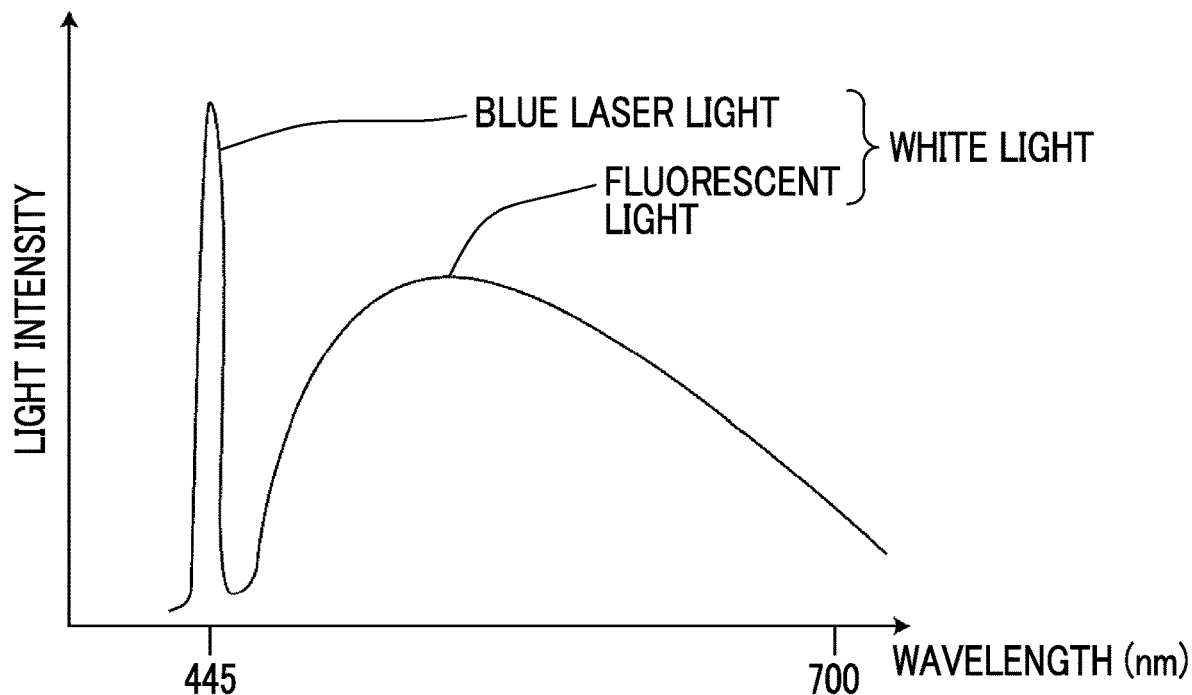
FIG. 3A is a graph illustrating the spectral intensity of white light.
Figure 3B:
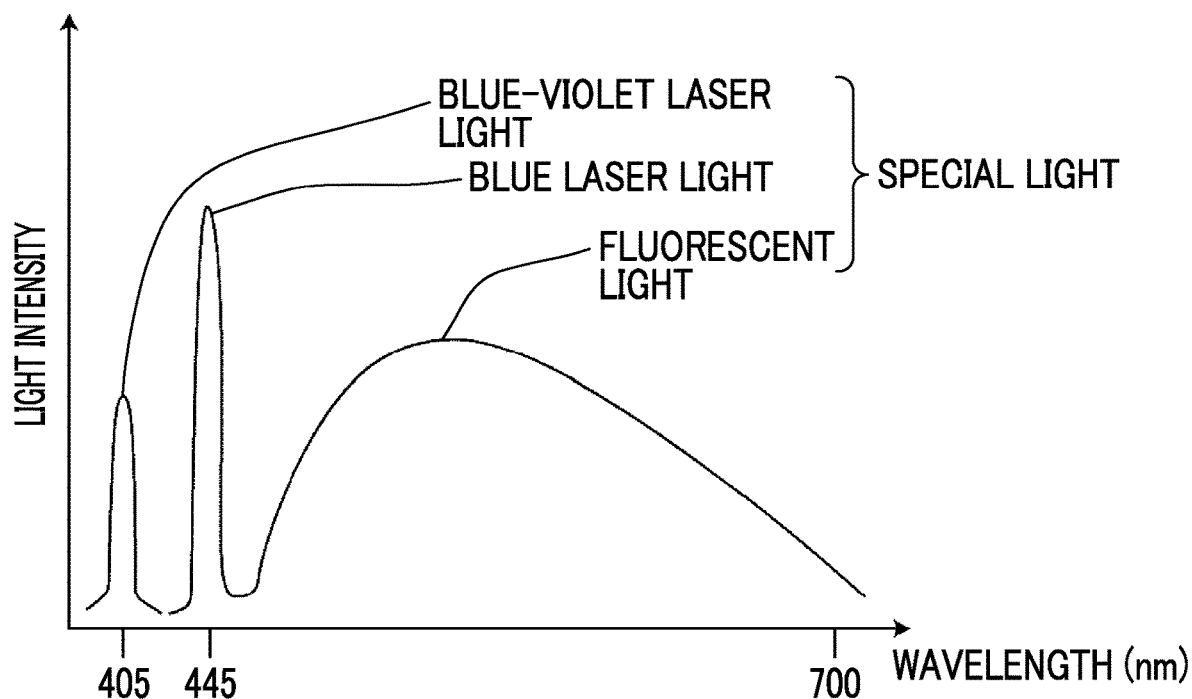
FIG. 3B is a graph illustrating the spectral intensity of special light.

Here, in the normal observation mode, the blue laser light is mainly incident on the phosphor 44. Therefore, the specimen is irradiated with white light obtained by combining the blue laser light and the fluorescent light emitted from the phosphor 44 excited by the blue laser light as illustrated in FIG. 3A. In contrast, in the special observation mode, both the blue-violet laser light and the blue laser light are incident on the phosphor 44. Therefore, the specimen is irradiated with special light obtained by combining the blue-violet laser light, the blue laser light, and the fluorescent light emitted from the phosphor 44 excited by the blue laser light as illustrated in FIG. 3B. In the special observation mode, since a blue component includes blue-violet laser light in addition to blue laser light with high emission intensity, the special light is broadband light that includes a large amount of blue component and has a wavelength range which is substantially the same as the entire visible light range.

It is preferable to use, as the phosphor 44, a phosphor including a plurality of kinds of phosphors (for example, a yttrium aluminum garnet (YAG)-based phosphor or a phosphor, such as BAM ($BaMgAl_{10}O_{17}$)) that absorb a portion of blue laser light and are excited to emit green to yellow light beams. In a case in which the semiconductor light emitting element is used as the excitation light source of the phosphor 44 as in this configuration example, high-intensity white light can be obtained with high emission efficiency and it is possible to easily adjust the intensity of white light. Therefore, it is possible to reduce a change in the color temperature and chromaticity of white light.

As illustrated in FIG. 2, the imaging optical system 24b of the endoscope 12 includes an imaging lens 46, the zooming lens 47, and an image sensor 48. Light reflected from the specimen is incident on the image sensor 48 through the imaging lens 46 and the zooming lens 47. Then, a reflection image of the specimen is formed on the image sensor 48. The zoom operation portion 22c is operated to move the zooming lens 47 between a telephoto end and a wide end. In a case in which the zooming lens 47 is moved to the wide end, the reflection image of the specimen is minified. The zooming lens 47 is moved to the telephoto end to enlarge the reflection image of the specimen.

The image sensor 48 is a color image sensor, captures the reflection image of the specimen, and outputs an image signal. For example, it is preferable that the image sensor 48 is a charge coupled device (CCD) image sensor or a complementary metal-oxide semiconductor (CMOS) image sensor. The image sensor used in the invention is an RGB image sensor that has RGB channels (ch) and has RGB color filters provided on an imaging surface. A red (R) image signal, a green (G) image signal, and a blue (B) image signal are output from an R pixel provided with an R color filter, a G pixel provided with a G color filter, and a B pixel provided with a B color filter by photoelectric conversion in each channel, respectively.

In addition, the image sensor 48 may be an image sensor in which CMYG filters (C: cyan, M: magenta, Y: yellow, and G: green) are provided on an imaging surface. In a case in which the image sensor with the CMYG filters is used, RGB image signals of three colors can be obtained from CMYG image signals of four colors by color conversion. In this case, it is necessary to provide color conversion means for converting the CMYG image signals of four colors into the RGB image signals of three colors into any one of the endoscope 12, the light source device 14, and the processor device 16.

The image signal output from the image sensor 48 is transmitted to a correlated double sampling (CDS)/automatic gain control (AGC) circuit 50. The CDS/AGC circuit 50 performs correlated double sampling (CDS) and automatic gain control (AGC) for the image signal which is an analog signal. A gamma conversion unit 51 performs gamma conversion for the image signal that has passed through the CDS/AGC circuit 50. Then, an image signal having gradation suitable for an output device, such as the monitor 18, is generated. An A/D converter 52 converts the image signal subjected to the gamma conversion into a digital image signal. The digital image signal subjected to the A/D conversion is input to the processor device 16.

The processor device 16 includes a receiving unit 54, an image processing switching unit 60, a normal light image processing unit 62, a special light image processing unit 64, and an image display signal generation unit 66. The receiving unit 54 receives the digital image signal from the endoscope 12. The receiving unit 54 includes a digital signal processor (DSP) 56 and a noise removal unit 58. The DSP 56 performs a gamma correction process and a color correction process for the digital image signal. The noise removal unit 58 performs a noise removal process (for example, a moving average method or a median filter method) for the digital image signal subjected to, for example, the gamma correction in the DSP 56 to remove noise from the digital image signal. The digital image signal from which noise has been removed is transmitted to the image processing switching unit 60.

In a case in which the normal observation mode is set by the mode switch 22b, the image processing switching unit 60 transmits the digital image signal to the normal light image processing unit 62. In a case in which the special observation mode is set, the image processing switching unit 60 transmits the digital image signal to the special light image processing unit 64.

The normal light image processing unit 62 includes a color conversion unit 68, a color enhancement unit 70, and a structure enhancement unit 72. The color conversion unit 68 assigns the input digital image signals of three RGB channels to R image data, G image data, and B image data, respectively, to convert the digital image signals into RGB image data. In addition, a color difference expansion process, such as 3×3 matrix processing, a gradation conversion process, or, three-dimensional LUT process, may be performed for the RGB image data.

The color enhancement unit 70 performs various types of color enhancement processes for the RGB image data. The structure enhancement unit 72 performs a structure enhancement process, such as spatial frequency enhancement, for the RGB image data. The RGB image data that has been subjected to the structure enhancement process in the structure enhancement unit 72 is input as the normal light image from the normal light image processing unit 62 to the image display signal generation unit 66.

The special light image processing unit 64 includes an inverse gamma conversion unit 74, an abnormal region enhancement unit 77, and a structure enhancement unit 78. The inverse gamma conversion unit 74 converts the digital image signal into RGB image data, similarly to the color conversion unit 68. The inverse gamma conversion unit 74 performs inverse gamma conversion for the input digital image signals of three RGB channels. Since the RGB image signals subjected to the inverse gamma conversion are reflectance-linear RGB signals which are linear relative to reflectance from the specimen, the reflectance-linear RGB signals include a large amount of various types of biological information (in this embodiment, information related to the atrophy of the stomach such as a change in the color of the stomach caused by the atrophic gastritis) of the specimen. The abnormal region enhancement unit 77 performs a color difference expansion process for enhancing a difference in color between a normal mucosal region (normal part) and an abnormal region (abnormal part) which is likely to include a site of lesion such as an atrophic mucosal part or a stomach cancer. The abnormal region enhancement unit 77 will be described in detail below. The structure enhancement unit 78 performs a structure enhancement process, such as spatial frequency enhancement, for the RGB image data subjected to the color difference expansion process. The RGB image data subjected to the structure enhancement process in the structure enhancement unit 78 is input as a special light image from the special light image processing unit 64 to the image display signal generation unit 66. An image acquisition unit according to the invention is formed by the inverse gamma conversion unit 74.

The image display signal generation unit 66 converts the normal light image input from the normal light image processing unit 62 or the special light image input from the special light image processing unit 64 into a display image signal which is to be displayed as an image that can be displayed on the monitor 18. The monitor 18 displays the normal light image or the special light image on the basis of the converted display image signal.

Figure 4:
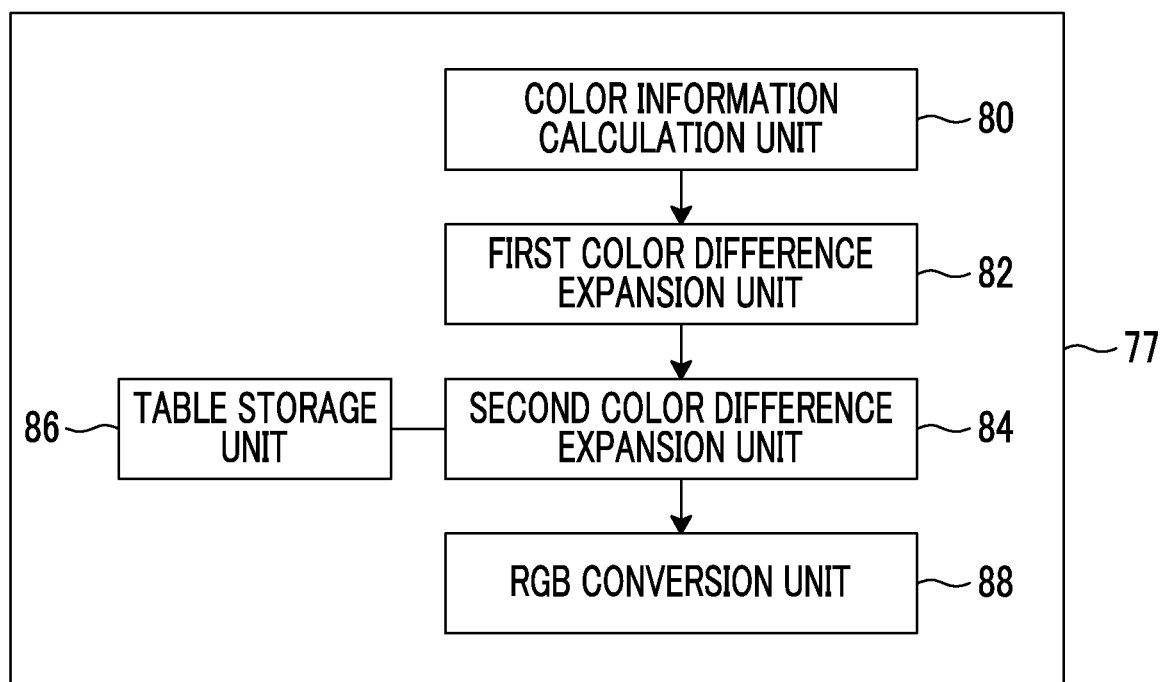
FIG. 4 is a block diagram illustrating the internal configuration of an abnormal region enhancement unit.

As illustrated in FIG. 4, the abnormal region enhancement unit 77 includes a color information calculation unit 80, a first color difference expansion unit 82, a second color difference expansion unit 84, a table storage unit 86, and an RGB conversion unit 88. In a case in which the gastric mucosa of the inner wall of the stomach in an endoscopic image is a normal part, blood vessels in a layer below the normal gastric mucosa can be hardly observed in the endoscopic image. In a case in which the gastric mucosa is an abnormal part such as atrophic mucosa, the number of gastric gland cells is reduced and a mucosal layer is thinned. As a result, muscularis mucosa of a color close to white is seen and the color of the abnormal part is more faded than the color of the normal part. However, in the endoscopic image of the stomach wall, the focus is put on a red part and tends to be put on a narrow range of a color space. Only a skillful observer can visually distinguish a difference in color between the normal gastric mucosa and the abnormal mucosa. For this reason, the color of the normal mucosa is used as a reference color and a color difference expansion process for expanding a color difference according to the difference between the color of each pixel of image data and the reference color is performed.

First, the color information calculation unit 80 calculates brightness or lightness, hue, and saturation from the R value, G value, and B value of each pixel of the RGB image data acquired by the inverse gamma conversion unit 74. An example of a color space having hue is an HSL color space having components, such as hue H, saturation S, and lightness L, as axes. However, the color space may be converted into any color space as long as it indicates brightness, hue, and saturation components. In addition, the RGB image data may be converted into a YCbCr image formed by a brightness signal Y and color difference signals Cb and Cr and brightness, hue, and saturation which are calculated from YCbCr by the following expressions may be used: hue $H=\mathrm{atan}(Cr/Cb)$; and saturation $S=\sqrt{(Cr^2+Cb^2)}$.

In the color difference expansion process, different conversion processes are performed for the hue and the brightness. The first color difference expansion unit 82 performs a conversion process for the hue and the second color difference expansion unit 84 performs a conversion process for the saturation. It is considered that there is no large change in the color of the mucosa in the hue direction depending on the luminance of light emitted, but there is a large difference in the color of the mucosa in the saturation direction depending on the brightness of light emitted. Therefore, the conversion process for the saturation varies depending on the brightness of each pixel.

The first color difference expansion unit 82 increases the difference between the hue of each pixel of the abnormal mucosa and the hue of each pixel of the normal mucosa, using the hue of the reference color as the center of expansion. Specifically, the first color difference expansion unit 82 changes the hue of each pixel such that a difference between a changed hue and the hue of the reference color is more than a difference between the original hue and the hue of the reference color. The hue of the pixel in the normal mucosa is close to the hue of the reference color. Therefore, in a case in which the hue of each pixel is matched with the hue of the reference color, the hue of the pixel is not changed and the hue gets further away from the original hue as it becomes closer to the hue appearing in the abnormal mucosa. In a case in which the hue of each pixel is closer to the positive direction (the hue of yellow) than the hue of the reference color (red), the original hue of each pixel is further moved in the positive direction. In a case in which the hue of each pixel is closer to the negative direction (the hue of magenta) than the hue of the reference color (red), the original hue of each pixel is further moved in the negative direction. In this way, the hue gets away from the reference color. However, in a case in which the difference in hue is large and the hue is distinctly different from the color of the normal mucosa, it is preferable to maintain the original hue without changing the hue. In a case in which the hue of each pixel is beyond the range of the hue appearing in the abnormal mucosa, the amount of movement from the original hue is reduced as the difference between the hue of each pixel and the hue of the reference color increases.

Figure 5:
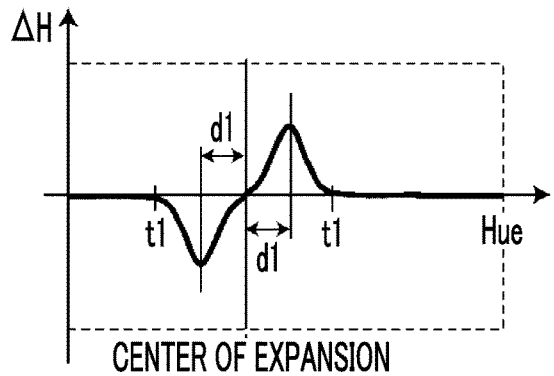
FIG. 5 is a diagram illustrating a relationship between the hue of each pixel and the amount of expansion of the hue and a relationship between the saturation of each pixel and the amount of expansion of the saturation.
Figure 5:
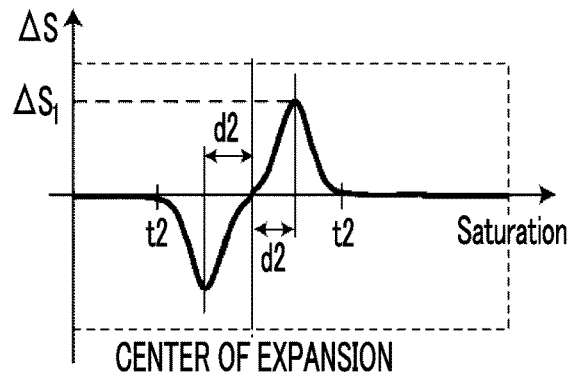
Figure 5:
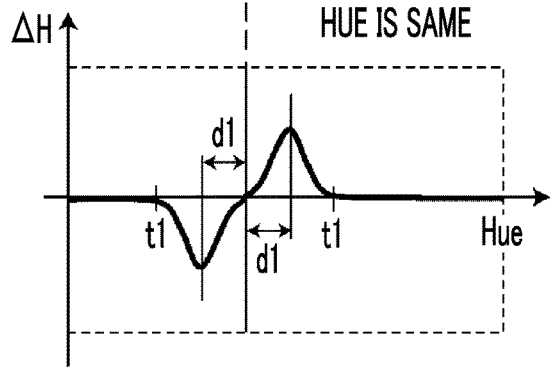
Figure 5:
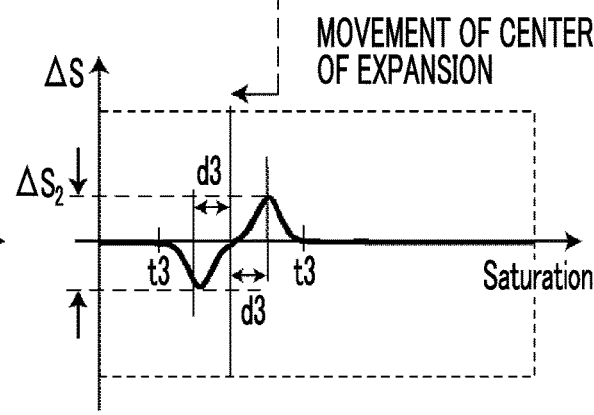

(A) and (C) of FIG. 5 illustrate the relationship between the hue H of each pixel and the amount of expansion ΔH of the hue. A first difference value d1 is a difference value between the hue appearing in the abnormal mucosa and the hue of the reference color. In a case in which the difference of the hue between the color of each pixel and the reference color is less than the first difference value d1, the amount of expansion ΔH of the hue increases as the difference the hue of each pixel and the hue of the reference color increases. In a case in which the hue difference is greater than the first difference value d1, the amount of expansion ΔH of the hue is reduced as the difference between the hue of each pixel and the hue of the reference color increases. In addition, in a case in which the difference of the hue between the color of each pixel and the reference color is beyond a first range t1, the hue difference is large and the color is determined to be different from the color of the normal mucosa. In the part in which the difference of the hue between the color of each pixel and the reference color is beyond the first range t1, the hue is not changed. (A) of FIG. 5 illustrates the relationship between the hue H of each pixel and the amount of expansion ΔH of the hue in a case in which brightness is high and (C) of FIG. 5 illustrates the relationship between the hue H of each pixel and the amount of expansion ΔH of the hue in a case in which brightness is low. Since the reference color has the same hue depending on brightness, there is no difference between (A) and (C) of FIG. 5. In a case in which the hue of the reference color varies depending on brightness, that is, the hue of the reference color is not the same at different brightness values, the hue of the reference color may be corrected so as to be the same at each brightness value.

In the hue conversion, a hue-hue conversion table in which the relationship between the hue H of each pixel and the amount of expansion ΔH of the hue is defined is stored in the table storage unit 86, the amount of expansion ΔH corresponding to the hue H of each pixel is extracted, and a hue H+ΔH subjected to the color difference expansion process is calculated. The table that has been stored in advance is used considering the calculation time. However, the relationship between the hue of each pixel and the hue of the reference color may be determined and the amount of expansion ΔH of the hue of each pixel may be frequently calculated.

The second color difference expansion unit 84 increases the difference between the saturation of each pixel of the abnormal mucosa and the saturation of each pixel of the normal mucosa, using the saturation of the reference color as the center of expansion. Specifically, the second color difference expansion unit 84 changes the saturation of each pixel such that a difference between a changed saturation and the saturation of the reference color is more than a difference between the original saturation and the saturation of the reference color. The saturation of the pixels in the normal mucosa is close to the saturation of the reference color. Therefore, in a case in which the saturation of each pixel is matched with the saturation of the reference color, the saturation of the pixel is not changed and the saturation gets further away from the original saturation as it becomes closer to the saturation appearing in the abnormal mucosa. That is, in a case in which the saturation of each pixel is higher than that of the reference color, the saturation is further increased. In a case in which the saturation of each pixel is lower than that of the reference color, the saturation is further decreased. However, in a case in which a difference in saturation is large and the saturation is distinctly different from the saturation of the color of the normal mucosa, it is preferable to maintain the original saturation without changing the saturation. In a case in which the saturation of each pixel is beyond the range of the saturation appearing in the abnormal mucosa, the amount of movement from the original hue is reduced as the difference between the saturation of each pixel and the saturation of the reference color increases.

However, in a bright image and a dark image, the saturation of the reference color increases as brightness increases and is reduced as brightness decreases. In addition, since a color gamut is narrowed as the bright image changes toward the dark image, a difference between the saturation of the color of the abnormal mucosa and the saturation of the reference color is reduced. Therefore, the saturation of the reference color is determined according to the brightness of each pixel. The saturation of the reference color increases as the brightness of each pixel increases. The saturation of the reference color decreases as the brightness of each pixel decreases. In addition, in a case in which the amount of expansion is large in a low-brightness image portion with a narrow color gamut, discomfort occurs. Therefore, it is preferable that the peak of the amount of expansion increases as the saturation of the reference color increases and decreases as the saturation of the reference color decreases. It is preferable that, as the maximum saturation of the same hue as that of the normal mucosa at the brightness of each pixel increases, the saturation of the reference color increases and the peak of the amount of expansion of the saturation increases. It is preferable that, as the maximum saturation decreases, the saturation of the reference color decreases and the peak of the amount of expansion of the saturation decreases.

(B) and (D) of FIG. 5 illustrate the relationship between the saturation S of each pixel and the amount of expansion ΔS of the saturation. Second difference values d2 and d3 indicate a difference between the saturation appearing in the abnormal mucosa and the saturation of the reference color. In a case in which the difference of the saturation between the color of each pixel and the reference color is less than the second difference values d2 and d3, as the saturation difference increases, the amount of saturation that gets away from the original saturation increases. In a case in which the saturation difference is greater than the second difference values d2 and d3, as the saturation difference increases, the amount of saturation that gets away from the original saturation is reduced. That is, the amount of expansion reaches a peak at the difference values d2 and d3. In a case in which the difference of the saturation between the color of each pixel and the reference color is beyond second ranges t2 and t3, the saturation difference is large and the color is determined to be different from the color of the normal mucosa. In the part in which the difference of the saturation between the color of each pixel and the reference color is beyond the second ranges t2 and t3, the saturation is not changed.

(B) of FIG. 5 illustrates the relationship between the saturation S of each pixel and the amount of expansion ΔS of the saturation in a case in which brightness is high and (D) of FIG. 5 illustrates the relationship between the saturation S of each pixel and the amount of expansion ΔS of the saturation in a case in which brightness is low. In a case in which brightness is high, the saturation of the reference color which is the center of expansion is high and the maximum amount of change ($\Delta S_1$) from the original saturation is set to a large value. In a case in which brightness is low, the center of expansion is moved to reduce the saturation of the reference color and the maximum amount of change ($\Delta S_2$) from the original saturation is set to be less than $\Delta S_1$. In addition, in a case in which brightness is high, since the difference between the saturation of a color appearing in the abnormal mucosa and the saturation of the reference color increases, the second difference value d2 is increased. In a case in which brightness is low, since the difference between the saturation of the color appearing in the abnormal mucosa and the saturation of the reference color tends to be reduced, the second difference value d3 is reduced. It is considered that the expansion range of the saturation difference (that is, the second ranges t2 and t3) is wide in a case in which brightness is high. Therefore, the second range t2 is set to a wide range. It is considered that the range is narrow in a case in which brightness is low. Therefore, the second range t3 is set to a narrow range.

In the saturation conversion, a plurality of saturation-saturation conversion tables are stored in advance according to different brightness values and the amount of expansion corresponding to the brightness is calculated. For example, a saturation-saturation conversion table in which the relationship between the saturation S of each pixel and the amount of expansion ΔS of the saturation in a case in which the brightness has a high value $L_{High}$ is defined and a saturation-saturation conversion table in which the relationship between the saturation S of a pixel and the amount of expansion ΔS of the saturation in a case in which the brightness has a low value $L_{Low}$ is defined are stored in the table storage unit 86 in advance. The amount of expansion $\Delta S_{High}$ corresponding to the saturation S of the pixel is extracted from the saturation-saturation conversion table for the high brightness $L_{High}$ and the amount of expansion $\Delta S_{Low}$ corresponding to the saturation S of the pixel is extracted from the saturation-saturation conversion table for the low brightness $L_{Low}$. Then, an expansion process is performed using a value obtained by interpolating the amounts of expansion $\Delta S_{High}$ and $\Delta S_{Low}$ according to the brightness value of the pixel. For example, in a case in which the amount of expansion calculated by the interpolation is $(\alpha \Delta S_{High} + \beta \Delta S_{Low})/(\alpha+\beta)$ (here, α and β indicate weights), the converted saturation is $S+(\alpha \Delta S_{High}+\beta \Delta S_{Low})/(\alpha+\beta)$. Alternatively, a plurality of saturation-saturation conversion tables corresponding to various brightness values may be prepared and the expansion process may be performed using a saturation-saturation conversion table corresponding to brightness close to the brightness of the pixel to calculate the saturation.

In addition, the brightness of each pixel may be calculated from the average of the brightness values of pixels in a predetermined pixel range having the pixel as the center. For example, the brightness value of a pixel that is at the center in 3×3 pixels is determined from the average of the brightness of the 3×3 neighboring pixels and saturation corresponding to the brightness is calculated. Alternatively, a low-resolution image may be created from an endoscopic image and the brightness of each pixel in the low-resolution image which is present at a position corresponding to each pixel of the endoscopic image may be determined as the brightness value of each pixel of the endoscopic image. As such, since the brightness of neighboring pixels is considered, it is possible to reduce the influence of, for example, noise that occurs in some pixels.

The first color difference expansion unit 82 does not change the hue of the reference color and the hue-hue conversion table even in a case in which the brightness value of each pixel is changed. However, the second color difference expansion unit 84 changes the brightness of the reference color and the saturation-saturation conversion table depending on the brightness value. Therefore, it is possible to perform conversion without discomfort even in a case in which the color gamut is changed by brightness. In particular, in a case in which a tubular structure is captured, since a part that is in front of the tubular structure in the depth direction is close to the light source, the image of the part becomes a bright image. However, since a part that is behind the tubular structure in the depth direction is far away from the light source, the image of the part becomes a dark image. The color gamut of the dark image is narrow. Therefore, in a case in which the same correction as that for the bright image is performed for the dark image, the color is slightly changed by the structure or the edge is distorted, which makes it difficult to easily see the image. For this reason, in a low-brightness image, as illustrated in (D) of FIG. 5, the center of expansion of the saturation (the saturation of the reference color) is lowered according to the brightness value. In addition, the peak $\Delta S_2$ of the amount of expansion is reduced and the range (second range t3) in which the amount of expansion is given is narrowed. Therefore, it is possible to enhance a structure in a dark part.

As described above, in a case in which the color of each pixel is close to the color of the abnormal mucosa, the amount of expansion is increased to a peak to expand the difference between the color of the abnormal mucosa and the color (reference color) of the normal mucosa and a color that is distinctly different from the color of the normal mucosa part of the normal mucosa is not changed. Therefore, it is easy to recognize an abnormal part and it is possible to observe the original color of a normal part, such as a normal mucosa, or a portion in which a part other than the mucosa is captured.

The RGB conversion unit 88 maintains the original brightness of each pixel of the endoscopic image and converts the hue obtained by the first color difference expansion unit 82 and the saturation obtained by the second color difference expansion unit 84 into RGB values to acquire RGB image data. In addition, the RGB conversion unit 88 performs gamma conversion for the RGB image data if necessary. Then, the RGB image data which has been subjected to color difference enhancement and has gradation suitable for an output device, such as the monitor 18, is obtained. In addition, an output unit according to the invention includes the RGB conversion unit 88 and the image display signal generation unit 66.

Figure 6:
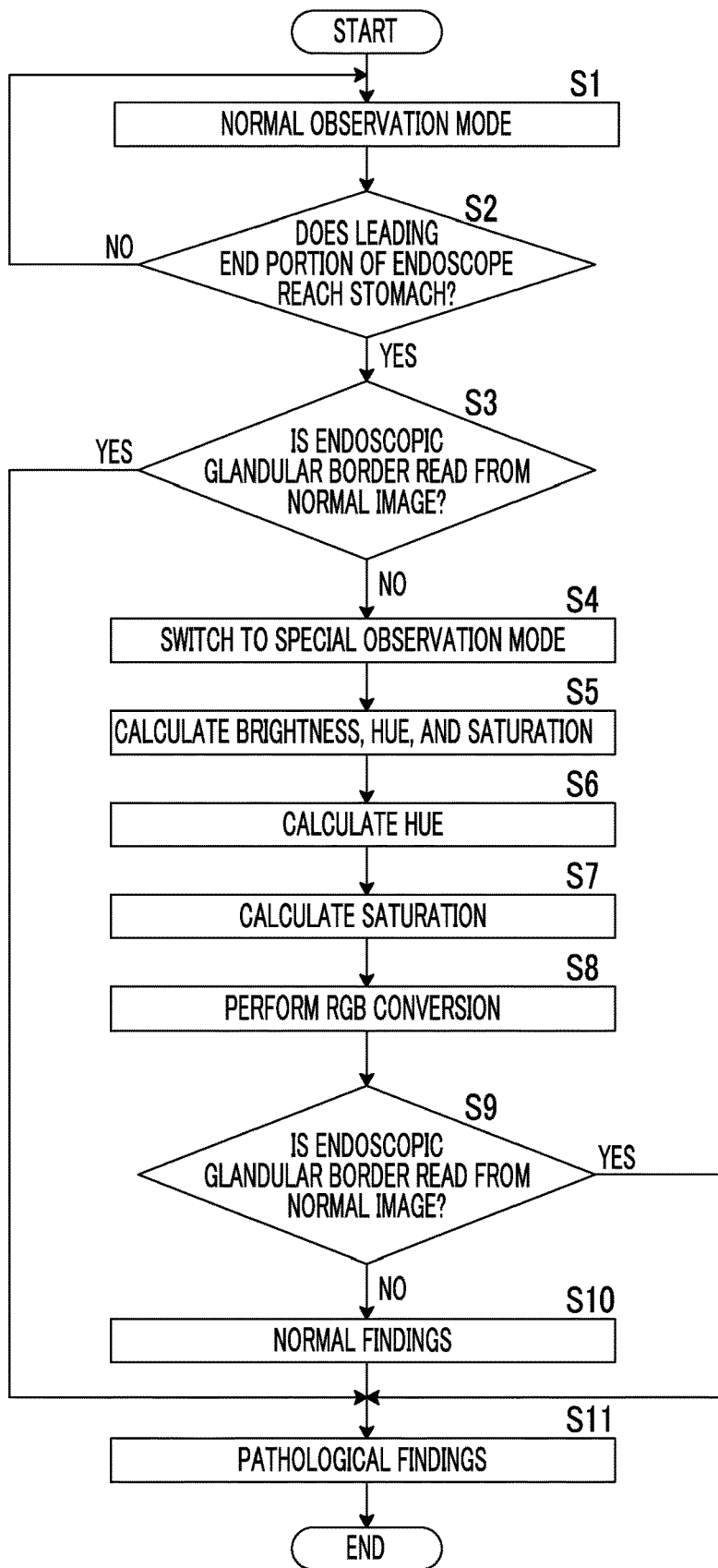
FIG. 6 is a flowchart illustrating the diagnosis flow of atrophic gastritis.

Next, a series of processes in this embodiment will be described with reference to the flowchart illustrated in FIG. 6. First, the normal observation mode is set (S1) and the insertion portion 21 of the endoscope 12 is inserted into a specimen. The leading end portion 24 is inserted into the specimen while a normal light image is observed (S2—N). In a case in which the leading end portion 24 of the insertion portion 21 reaches the stomach (S2—Y), it is diagnosed whether the atrophic gastritis is present (S3). Here, in a case in which the fading of the color of the mucosa or a border (referred to as an endoscopic glandular border) between a part through which dendritic deep blood vessels are seen and a part through which the dendritic deep blood vessels are not seen can be read from the normal light image (S3—Y), a doctor determines it as the pathologic findings indicating the emergence of a lesion, such as a stomach cancer, caused by the atrophic gastritis (S11).

In a case in which it is difficult to read the faded mucosa or the presence of the endoscopic glandular border from the normal light image (S3—N), the mode switch 22b is operated to switch the mode to the special observation mode in order to diagnose more reliably (S4). Upon switching the mode to the special observation mode, special light including both of blue laser light and blue-violet laser light is emitted. The inverse gamma conversion unit 74 acquires RGB image data from an RGB image signal obtained in a case in which the special light is emitted.

First, the color information calculation unit 80 calculates brightness, hue, and saturation from the R value, G value, and B value of each pixel of the RGB image data (S5). The first color difference expansion unit 82 extracts the amount of expansion $\Delta H$ of the hue corresponding to the hue H of the pixel from the hue-hue conversion table for hue stored in the table storage unit 86 and calculates a converted hue $H+\Delta H$ (S6). Then, the second color difference expansion unit 84 calculates the saturation S of the reference color corresponding to the brightness of each pixel and the amount of expansion $\Delta S$ of the saturation corresponding to the brightness value, using the saturation-saturation conversion table for high brightness $L_{High}$ and the saturation-saturation conversion table for low brightness $L_{Low}$ stored in the table storage unit 86, and calculates a converted saturation $S+\Delta S$ (S7). The brightness of each pixel is maintained without being changed.

The RGB conversion unit 88 returns to an RGB color space on the basis of the image data in which color conversion in S5 to S7 has been performed for the entire image and a special light image is displayed on the monitor 18 (S8).

In a case in which there is no atrophy of the stomach, the mucosa is displayed in its normal color in the special light image. In this case (S9—N), the doctor determines it as normal findings indicating that a site of lesion, such as a stomach cancer, caused by the atrophic gastritis is absent (S10). In contrast, in a case in which there is a slight progress of the atrophy of the stomach, the atrophic mucosa is displayed in faded colors (S9—Y). In this way, it is possible to clearly display the endoscopic glandular border. Therefore, the doctor is able to determine it as the pathologic findings indicating that a lesion, such as a stomach cancer, caused by the atrophic gastritis is present even in a case in which the color of the atrophic mucosa is little faded in the actual stomach (S11).

In the above-described embodiment, the case in which special light including blue narrow-band light (blue laser light and blue-violet laser light) that is absorbed at a high rate by an absorbing material of the mucosa is used has been described. However, light including green narrow-band light (for example, a wavelength component of 540 nm to 560 nm) that is absorbed at a high rate by an absorbing material of the mucosa may be used.

In the above-described embodiment, the color expansion in the color space having the hue based on the reflectance-linear RGB signals has been described. However, the color expansion may be performed on the basis of lightness $L^*$, hue $H=\mathrm{atan}(b^*/a^*)$, and chroma $C^*=\sqrt{(a^{*2}+b^{*2})}$ of the International Commission on Illumination (CIE) $L^*a^*b^*$ color space having an axis close to an index of the perception of luminance by humans. In the above-described embodiment, the saturation conversion process varies depending on the brightness of each pixel. However, in the $L^*a^*b^*$ color space, since luminance is not represented by brightness, but is represented by lightness, the conversion process varies depending on the lightness. In addition, in the HSI color space according to the above-described embodiment, as brightness becomes higher, the range of saturation becomes wider and the maximum saturation is a high value. However, in the $L^*a^*b^*$ color space, in a case in which lightness is equal to or greater than a specific value, the range of chroma is gradually narrowed and the chroma $C^*$ is 0 at the maximum value ($L^*=100$). Therefore, in the $L^*a^*b^*$ color space, preferably, as the maximum chroma of the same color as the color of the normal mucosa at lightness becomes higher, the chroma of the reference color becomes higher and the peak of the amount of expansion of the chroma becomes higher. In addition, preferably, as the maximum chroma becomes lower, the chroma of the reference color becomes lower and the peak of the amount of expansion of the chroma becomes lower.

In the above-described embodiment, the case in which the light source is a semiconductor light emitting element has been described. However, in a second embodiment, an endoscope in which an LED is used as a light source will be described with reference to FIGS. 7 and 8. The configuration of the second embodiment is substantially the same as that of the first embodiment except a light source device 14 of the endoscope and an illumination optical system 24c of a leading end portion 24. Therefore, the same components denoted b the same reference numerals and the detailed description thereof will not be repeated. Since the operation of the endoscope and the flow of a process during examination are substantially the same as those in the first embodiment, the detailed description thereof will not be repeated.

Figure 7:
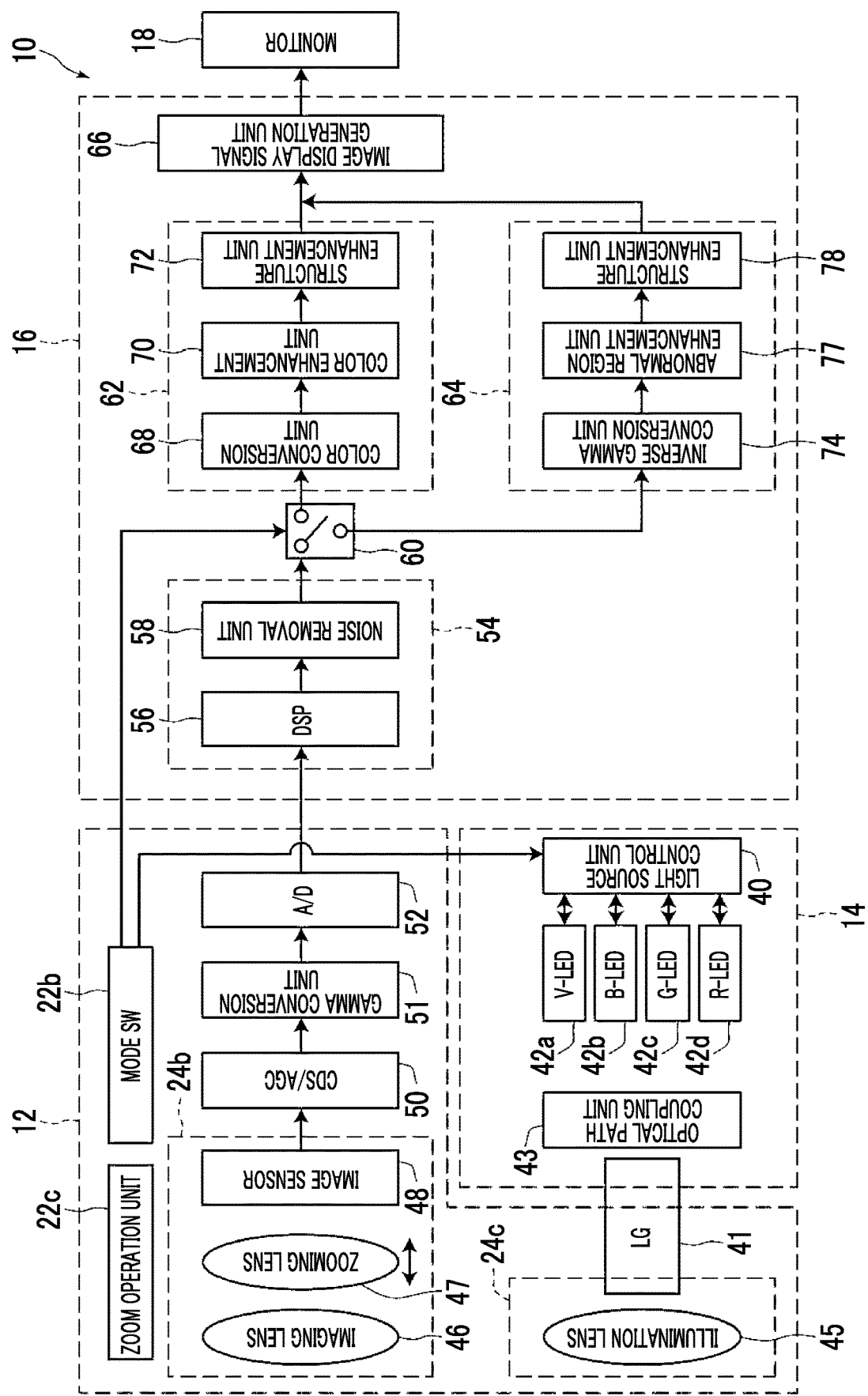
FIG. 7 is a block diagram illustrating the function of an endoscope system according to a second embodiment.

As illustrated in FIG. 7, the light source device 14 includes a violet light emitting diode (V-LED) 42a, a blue light emitting diode (B-LED) 42b, a green light emitting diode (G-LED) 42c, a red light emitting diode (R-LED) 42d, and a light source control unit 40 that controls the driving of the four color LEDs 42a to 42d. In this configuration, an optical path coupling unit 43 that couples the optical paths of four color light components emitted from the four color LEDs 42a to 42d. The inside of the subject is irradiated with the light coupled by the optical path coupling unit 43 through the light guide (LG) 41 and the illumination lens 45 inserted into the insertion portion 21. In addition, a laser diode (LD) may be used as the LED.

Figure 8:
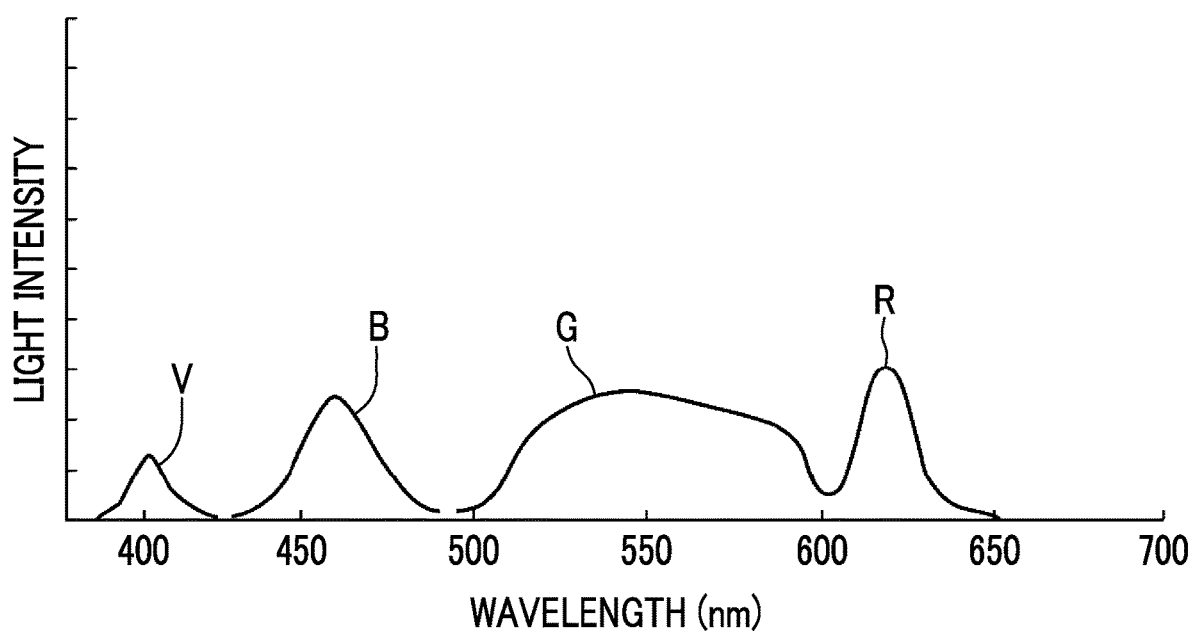
FIG. 8 is a graph illustrating the wavelength of a light source.

As illustrated in FIG. 8, the V-LED 42*a* generates violet light Vi that has a center wavelength of 405±10 nm and a wavelength range of 380 nm to 420 nm. The B-LED 42*b* generates blue light Bl that has a center wavelength of 460±10 nm and a wavelength range of 420 nm to 500 nm. The G-LED 42*c* generates green light Gr that has a wavelength range of 480 nm to 600 nm. The R-LED 42*d* generates red light Re that has a center wavelength 620 nm to 630 nm and a wavelength range of 600 nm to 650 nm.

The light source control unit 40 turns on the V-LED 42*a*, the B-LED 42*b*, the G-LED 42*c*, and the R-LED 42*d* in any of the normal observation mode and the special observation mode. Therefore, an observation target is irradiated with mixed light of the four color light components, that is, the violet light Vi, the blue light Bl, the green light Gr, and the red light Re. In addition, the light source control unit 40 controls the LEDs 42*a* to 42*d* such that the ratio of the amounts of violet light Vi, blue light Bl, green light Gr, and red light Re is $Vi_c:Bl_c:Gr_c:Re_c$ in the normal observation mode. In contrast, in the special observation mode, the light source control unit 40 controls the LEDs 42*a* to 42*d* such that the ratio of the amounts of violet light Vi, blue light Bl, green light Gr, and red light Re is $Vi_s:Bl_s:Ge_s:Re_s$.

The illumination optical system 24*c* and the imaging optical system 24*b* are provided in the leading end portion 24 of the endoscope 12. The illumination optical system 24*c* includes the illumination lens 45 and the observation target is irradiated with light from the light guide 41 through the illumination lens 45. The imaging optical system 24*b* has substantially the same configuration as that in the first embodiment.

In the first and second embodiments, the case in which the process of the abnormal region enhancement unit 77 is performed in the processor device 16 has been described. However, for the process of the abnormal region enhancement unit 77 in the processor device 16, an image processing program that causes a computer to function as the inverse gamma conversion unit, the color information calculation unit, the first color difference expansion unit, the second color difference expansion unit, and the display unit may be installed in an external computer and the external computer may perform the process of the abnormal region enhancement unit 77 for the endoscopic image recorded on, for example, an external recording unit attached to the processor device 16.

What is claimed is:

1. An image processing apparatus comprising:
   an image acquisition unit that acquires an endoscopic image formed by an image signal including a narrow-band image signal;
   a color information calculation unit that calculates brightness, hue, and saturation of each pixel of the endoscopic image;
   a first color difference expansion unit that changes the hue of each pixel of the endoscopic image such that a difference between a changed hue and the hue of a reference color indicating a normal part is more than a difference between an original hue and the hue of the reference color in a case in which a difference between the hue of the reference color and the hue of the pixel is within a first range and changes the hue of the pixel to the original hue in a case in which the hue of each pixel is matched with the hue of the reference color and a case in which the hue difference is beyond the first range;
   a second color difference expansion unit that changes the saturation of each pixel such that a difference between a changed saturation and the saturation of the reference color which is determined according to the brightness of each pixel of the endoscopic image is more than a difference between an original saturation and the saturation of the reference color in a case in which a difference between the saturation of the reference color and the saturation of the pixel is within a second range and changes the saturation of the pixel to the original saturation in a case in which the saturation of each pixel is matched with the saturation of the reference color and a case in which the saturation difference is beyond the second range; and
   an output unit that outputs an endoscopic image in which the brightness of each pixel is the original brightness and whose color has been changed to a color having the hue obtained by the first color difference expansion unit and the saturation obtained by the second color difference expansion unit.

2. The image processing apparatus according to claim 1, wherein the first color difference expansion unit increases an amount of expansion for changing the original hue of each pixel to the changed hue as the hue difference increases in a case in which the hue difference is less than a first difference value within the first range and decreases the amount of expansion for changing the original hue of each pixel to the changed hue as the hue difference increases in a case in which the hue difference is greater than the first difference value.

3. The image processing apparatus according to claim 1, wherein the second color difference expansion unit increases an amount of expansion for changing the original saturation of each pixel to the changed saturation as the saturation difference increases in a case in which the saturation difference is less than a second difference value within the second range and decreases the amount of expansion for changing the original saturation of each pixel to the changed saturation as the saturation difference increases in a case in which the saturation difference is greater than the second difference value.

4. The image processing apparatus according to claim 3, wherein, as the brightness of each pixel increases, the saturation of the reference color increases, and as the brightness of each pixel decreases, the saturation of the reference color decreases.

5. The image processing apparatus according to claim 4, wherein the amount of expansion for changing the original saturation of each pixel to the changed saturation reaches a peak in a case in which the saturation difference is the second difference value and the second color difference expansion unit increases the peak as the saturation of the reference color increases and decreases the peak as the saturation of the reference color decreases.

6. The image processing apparatus according to claim 4, wherein the second color difference expansion unit widens the second range as the saturation of the reference color increases and narrows the second range as the saturation of the reference color decreases.

7. The image processing apparatus according to claim 5, wherein the second color difference expansion unit widens the second range as the saturation of the reference color increases and narrows the second range as the saturation of the reference color decreases.

8. The image processing apparatus according to claim 1, wherein the hue of the reference color is constant even in a case in which a brightness value of each pixel varies.

9. The image processing apparatus according to claim 1, wherein the brightness of each pixel is an average of the brightness of pixels in a predetermined range having the pixel as a center.

10. The image processing apparatus according to claim 1, wherein the brightness of each pixel is calculated from the brightness of pixels which are present at positions corresponding to each pixel in a low-resolution image of the endoscopic image.

11. The image processing apparatus according to claim 1, wherein the narrow-band image signal is obtained by capturing an image of a specimen illuminated with narrow-band light which is absorbed by blood at a higher rate than light in other bands.

12. The image processing apparatus according to claim 1, wherein the narrow-band image signal is a blue narrow-band image signal obtained by capturing an image of a specimen illuminated with blue narrow-band light, which is absorbed by blood at a higher rate than light in other bands, in a blue band or a green narrow-band image signal obtained by capturing an image of a specimen illuminated with green narrow-band light, which is absorbed by blood at a higher rate than light in other bands, in a green band.

13. The image processing apparatus according to claim 1, wherein the endoscopic image is an image of an inner wall of a stomach,
the normal part is a normal mucosa, and
an abnormal part is an abnormal mucosa.

14. The image processing apparatus according to claim 1, wherein the first color difference expansion unit determines the hue of each pixel on the basis of a hue-hue conversion table in which a value for changing the original hue to the changed hue is defined, and
the second color difference expansion unit stores a plurality of saturation-saturation conversion tables, in which a value for changing the original saturation to the changed saturation is defined, according to different brightness values in advance and determines the saturation of each pixel on the basis of a saturation-saturation conversion table corresponding to the brightness of each pixel among the plurality of saturation-saturation conversion tables.

15. A method for operating an image processing apparatus comprising an image acquisition unit, a color information calculation unit, a first color difference expansion unit, a second color difference expansion unit, and an output unit, the method comprising:
an image acquisition step of allowing the image acquisition unit to acquire an endoscopic image formed by an image signal including a narrow-band image signal;
a color information calculation step of allowing the color information calculation unit to calculate brightness, hue, and saturation of each pixel of the endoscopic image;
a first color difference expansion step of allowing the first color difference expansion unit to change the hue of each pixel of the endoscopic image such that a difference between a changed hue and the hue of a reference color indicating a normal part is more than a difference between an original hue and the hue of the reference color in a case in which a difference between the hue of the reference color and the hue of the pixel is within a first range and to change the hue of the pixel to the original hue in a case in which the hue of each pixel is matched with the hue of the reference color and a case in which the hue difference is beyond the first range;
a second color difference expansion step of allowing the second color difference expansion unit to change the saturation of each pixel such that a difference between a changed saturation and the saturation of the reference color which is determined according to the brightness of each pixel of the endoscopic image is more than a difference between an original saturation and the saturation of the reference color in a case in which a difference between the saturation of the reference color and the saturation of the pixel is within a second range and to change the saturation of the pixel to the original saturation in a case in which the saturation of each pixel is matched with the saturation of the reference color and a case in which the saturation difference is beyond the second range; and
an output step of allowing the output unit to output an endoscopic image in which the brightness of each pixel is the original brightness and whose color has been changed to a color having the hue obtained by the first color difference expansion unit and the saturation obtained by the second color difference expansion unit.

16. A non-transitory computer-readable recording medium storing therein an image processing program that causes a computer to function as:
an image acquisition unit that acquires an endoscopic image formed by an image signal including a narrow-band image signal;
a color information calculation unit that calculates brightness, hue, and saturation of each pixel of the endoscopic image;
a first color difference expansion unit that changes the hue of each pixel of the endoscopic image such that a difference between a changed hue and the hue of a reference color indicating a normal part is more than a difference between an original hue and the hue of the reference color in a case in which a difference between the hue of the reference color and the hue of the pixel is within a first range and changes the hue of the pixel to the original hue in a case in which the hue of each pixel is matched with the hue of the reference color and a case in which the hue difference is beyond the first range;
a second color difference expansion unit that changes the saturation of each pixel such that a difference between a changed saturation and the saturation of the reference color which is determined according to the brightness of each pixel of the endoscopic image is more than a difference between an original saturation and the saturation of the reference color in a case in which a difference between the saturation of the reference color and the saturation of the pixel is within a second range and changes the saturation of the pixel to the original saturation in a case in which the saturation of each pixel is matched with the saturation of the reference color and a case in which the saturation difference is beyond the second range; and
an output unit that outputs an endoscopic image in which the brightness of each pixel is the original brightness and whose color has been changed to a color having the hue obtained by the first color difference expansion unit and the saturation obtained by the second color difference expansion unit.

17. An image processing apparatus comprising:
an image acquisition unit that acquires an endoscopic image formed by an image signal including a narrow-band image signal;
a color information calculation unit that calculates brightness, hue, and saturation of each pixel of the endoscopic image;
a first color difference expansion unit that (i) changes the hue of each pixel of the endoscopic image such that a difference between a changed hue and the hue of a reference color indicating a normal part is more than a difference between an original hue and the hue of the reference color in a case in which a difference between the hue of the reference color and the hue of the pixel is within a first range and changes the hue of the pixel to the original hue in a case in which the hue of each pixel is matched with the hue of the reference color and a case in which the hue difference is beyond the first range, and (ii) increases an amount of expansion for changing the original hue of each pixel to the changed hue as the hue difference increases in a case in which the hue difference is less than a first difference value, which is a difference in hue between an abnormal part and the normal part, within the first range and decreases the amount of expansion for changing the original hue of each pixel to the changed hue as the hue difference increases in a case in which the hue difference is greater than the first difference value;
a second color difference expansion unit that (i) changes the saturation of each pixel such that a difference between a changed saturation and the saturation of the reference color which is determined according to the brightness of each pixel of the endoscopic image is more than a difference between an original saturation and the saturation of the reference color in a case in which a difference between the saturation of the reference color and the saturation of the pixel is within a second range and changes the saturation of the pixel to the original saturation in a case in which the saturation of each pixel is matched with the saturation of the reference color and a case in which the saturation difference is beyond the second range, and (ii) increases an amount of expansion for changing the original saturation of each pixel to the changed saturation as the saturation difference increases in a case in which the saturation difference is less than a second difference value, which is a difference in saturation between the abnormal part and the normal part, within the second range and decreases the amount of expansion for changing the original saturation of each pixel to the changed saturation as the saturation difference increases in a case in which the saturation difference is greater than the second difference value; and
an output unit that outputs an endoscopic image in which the brightness of each pixel is the original brightness and whose color has been changed to a color having the hue obtained by the first color difference expansion unit and the saturation obtained by the second color difference expansion unit,
wherein, as the brightness of each pixel increases, the saturation of the reference color increases,
as the brightness of each pixel decreases, the saturation of the reference color decreases, and
the amount of expansion for changing the original saturation of each pixel to the changed saturation reaches a peak in a case in which the saturation difference is the second difference value and the second color difference expansion unit increases the peak as the saturation of the reference color increases and decreases the peak as the saturation of the reference color decreases.

18. A method for operating an image processing apparatus comprising an image acquisition unit, a color information calculation unit, a first color difference expansion unit, a second color difference expansion unit, and an output unit, the method comprising:
an image acquisition step of allowing the image acquisition unit to acquire an endoscopic image formed by an image signal including a narrow-band image signal;
a color information calculation step of allowing the color information calculation unit to calculate brightness, hue, and saturation of each pixel of the endoscopic image;
a first color difference expansion step of allowing the first color difference expansion unit (i) to change the hue of each pixel of the endoscopic image such that a difference between a changed hue and the hue of a reference color indicating a normal part is more than a difference between an original hue and the hue of the reference color in a case in which a difference between the hue of the reference color and the hue of the pixel is within a first range and to change the hue of the pixel to the original hue in a case in which the hue of each pixel is matched with the hue of the reference color and a case in which the hue difference is beyond the first range and (ii) to increase an amount of expansion for changing the original hue of each pixel to the changed hue as the hue difference increases in a case in which the hue difference is less than a first difference value, which is a difference in hue between an abnormal part and the normal part, within the first range and to decrease the amount of expansion for changing the original hue of each pixel to the changed hue as the hue difference increases in a case in which the hue difference is greater than the first difference value;
a second color difference expansion step of allowing the second color difference expansion unit (i) to change the saturation of each pixel such that a difference between a changed saturation and the saturation of the reference color which is determined according to the brightness of each pixel of the endoscopic image is more than a difference between an original saturation and the saturation of the reference color in a case in which a difference between the saturation of the reference color and the saturation of the pixel is within a second range and to change the saturation of the pixel to the original saturation in a case in which the saturation of each pixel is matched with the saturation of the reference color and a case in which the saturation difference is beyond the second range, and (ii) to increase an amount of expansion for changing the original saturation of each pixel to the changed saturation as the saturation difference increases in a case in which the saturation difference is less than a second difference value, which is a difference in saturation between the abnormal part and the normal part, within the second range and to decrease the amount of expansion for changing the original saturation of each pixel to the changed saturation as the saturation difference increases in a case in which the saturation difference is greater than the second difference value; and
an output step of allowing the output unit to output an endoscopic image in which the brightness of each pixel is the original brightness and whose color has been changed to a color having the hue obtained by the first color difference expansion unit and the saturation obtained by the second color difference expansion unit, wherein, as the brightness of each pixel increases, the saturation of the reference color increases, as the brightness of each pixel decreases, the saturation of the reference color decreases, and in the second color difference expansion step, the amount of expansion for changing the original saturation of each pixel to the changed saturation reaches a peak in a case in which the saturation difference is the second difference value and the peak increases as the saturation of the reference color increases and decreases as the saturation of the reference color decreases.

19. A non-transitory computer-readable recording medium storing therein an image processing program that causes a computer to function as:

an image acquisition unit that acquires an endoscopic image formed by an image signal including a narrow-band image signal;

a color information calculation unit that calculates brightness, hue, and saturation of each pixel of the endoscopic image;

a first color difference expansion unit that (i) changes the hue of each pixel of the endoscopic image such that a difference between a changed hue and the hue of a reference color indicating a normal part is more than a difference between an original hue and the hue of the reference color in a case in which a difference between the hue of the reference color and the hue of the pixel is within a first range and changes the hue of the pixel to the original hue in a case in which the hue of each pixel is matched with the hue of the reference color and a case in which the hue difference is beyond the first range, and (ii) increases an amount of expansion for changing the original hue of each pixel to the changed hue as the hue difference increases in a case in which the hue difference is less than a first difference value, which is a difference in hue between an abnormal part and the normal part, within the first range and decreases the amount of expansion for changing the original hue of each pixel to the changed hue as the hue difference increases in a case in which the hue difference is greater than the first difference value;

a second color difference expansion unit that (i) changes the saturation of each pixel such that a difference between a changed saturation and the saturation of the reference color which is determined according to the brightness of each pixel of the endoscopic image is more than a difference between an original saturation and the saturation of the reference color in a case in which a difference between the saturation of the reference color and the saturation of the pixel is within a second range and changes the saturation of the pixel to the original saturation in a case in which the saturation of each pixel is matched with the saturation of the reference color and a case in which the saturation difference is beyond the second range, and (ii) increases an amount of expansion for changing the original saturation of each pixel to the changed saturation as the saturation difference increases in a case in which the saturation difference is less than a second difference value, which is a difference in saturation between the abnormal part and the normal part, within the second range and decreases the amount of expansion for changing the original saturation of each pixel to the changed saturation as the saturation difference increases in a case in which the saturation difference is greater than the second difference value; and an output unit that outputs an endoscopic image in which the brightness of each pixel is the original brightness and whose color has been changed to a color having the hue obtained by the first color difference expansion unit and the saturation obtained by the second color difference expansion unit, wherein, as the brightness of each pixel increases, the saturation of the reference color increases, as the brightness of each pixel decreases, the saturation of the reference color decreases, and the amount of expansion for changing the original saturation of each pixel to the changed saturation reaches a peak in a case in which the saturation difference is the second difference value and the second color difference expansion unit increases the peak as the saturation of the reference color increases and decreases the peak as the saturation of the reference color decreases.

* * * * *